(12) United States Patent
Gormley

(10) Patent No.: US 12,592,301 B2
(45) Date of Patent: Mar. 31, 2026

(54) PROMPT ENGINEERING AND GENERATIVE AI FOR GOAL-BASED IMAGERY

(71) Applicant: The Toronto-Dominion Bank, Toronto (CA)

(72) Inventor: Breena Patricia Gormley, Toronto (CA)

(73) Assignee: The Toronto-Dominion Bank, Toronto (CA)

( * ) Notice: Subject to any disclaimer, the term of this patent is extended or adjusted under 35 U.S.C. 154(b) by 196 days.

(21) Appl. No.: 18/240,269

(22) Filed: Aug. 30, 2023

(65) Prior Publication Data

US 2025/0078972 A1      Mar. 6, 2025

(51) Int. Cl.
| | |
|---|---|
| *G06T 11/60* | (2006.01) |
| *G06N 3/0475* | (2023.01) |
| *G16H 20/00* | (2018.01) |
| *G16H 50/20* | (2018.01) |

(52) U.S. Cl.
CPC ........... *G16H 20/00* (2018.01); *G06N 3/0475* (2023.01); *G06T 11/60* (2013.01); *G16H 50/20* (2018.01); *G06T 2200/24* (2013.01)

(58) Field of Classification Search
None
See application file for complete search history.

(56) References Cited

U.S. PATENT DOCUMENTS

| | | | |
|---|---|---|---|
| 9,864,982 B2 | 1/2018 | Bristow et al. | |
| 10,163,085 B2 | 12/2018 | D'Agostino et al. | |

| | | | |
|---|---|---|---|
| 10,178,246 B1 | 1/2019 | Horvath et al. | |
| 10,181,114 B2 | 1/2019 | Tseretopoulos et al. | |
| 10,339,931 B2 | 7/2019 | Tseretopoulos et al. | |
| 10,346,824 B2 | 7/2019 | Chan et al. | |
| 10,360,303 B2 | 7/2019 | Volkovs et al. | |
| 10,405,146 B1 | 9/2019 | Kuruvilla et al. | |
| 10,438,206 B2 | 10/2019 | Jivraj et al. | |
| 10,440,196 B2 | 10/2019 | Horvath et al. | |
| 10,440,197 B2 | 10/2019 | Horvath et al. | |
| 10,460,748 B2 | 10/2019 | Tseretopoulos et al. | |
| 10,482,675 B1 | 11/2019 | Sutter et al. | |
| 10,659,400 B2 | 5/2020 | Moon et al. | |
| 10,698,902 B2 | 6/2020 | Tseretopoulos et al. | |
| 10,706,635 B2 | 7/2020 | Sutter et al. | |

(Continued)

OTHER PUBLICATIONS

1. Virvou M. Artificial Intelligence and User Experience in reciprocity: Contributions and state of the art. Intelligent Decision Technologies. 2023; 17(1):73-125. doi: 10.3233/IDT-230092 (Year: 2023).*

(Continued)

*Primary Examiner* — Robert A Sorey

(57)      ABSTRACT

An example operation may include one or more of storing a generative artificial intelligence (GenAI) model configured to create images, displaying a plurality of prompts on a user interface of a software application, receiving an identifier of a goal of the user and attributes of the goal via the plurality of prompts on the user interface, executing the GenAI model on the identifier of the goal of the user and the attributes of the goal to generate a custom image of the goal for the user, and displaying the custom image of the goal via the user interface of the software application.

20 Claims, 22 Drawing Sheets

(56) References Cited

U.S. PATENT DOCUMENTS

| | | |
|---|---|---|
| 10,708,721 B2 | 7/2020 | Kuruvilla et al. |
| 10,728,259 B2 | 7/2020 | McCarter et al. |
| 10,776,619 B2 | 9/2020 | Collinson et al. |
| 10,795,701 B2 | 10/2020 | Myers |
| 10,824,941 B2 | 11/2020 | Volkovs et al. |
| 10,831,923 B2 | 11/2020 | Dunjic et al. |
| 10,832,047 B2 | 11/2020 | Moghtadai |
| 10,862,897 B2 | 12/2020 | D'Agostino et al. |
| 10,867,292 B2 | 12/2020 | Lin et al. |
| 10,867,293 B2 | 12/2020 | Bristow et al. |
| 10,878,816 B2 | 12/2020 | Tseretopoulos et al. |
| 10,902,220 B2 | 1/2021 | Lozon et al. |
| 10,922,665 B2 | 2/2021 | Miller et al. |
| 10,943,605 B2 | 3/2021 | Tseretopoulos et al. |
| 10,977,617 B2 | 4/2021 | Tseretopoulos et al. |
| 11,004,187 B2 | 5/2021 | Kuruvilla et al. |
| 11,017,028 B2 | 5/2021 | Dunjic et al. |
| 11,017,466 B1 | 5/2021 | Cunningham et al. |
| 11,030,415 B2 | 6/2021 | Volkovs et al. |
| 11,055,924 B2 | 7/2021 | Navarro et al. |
| 11,061,638 B2 | 7/2021 | Lam |
| 11,070,448 B2 | 7/2021 | Miller et al. |
| 11,087,314 B2 | 8/2021 | Gandhi et al. |
| 11,100,168 B2 | 8/2021 | Miller et al. |
| 11,140,143 B2 | 10/2021 | Moon et al. |
| 11,144,921 B2 | 10/2021 | Dunjic et al. |
| 11,144,998 B2 | 10/2021 | Kuruvilla et al. |
| 11,145,169 B2 | 10/2021 | Pratten et al. |
| 11,182,860 B2 | 11/2021 | Kuruvilla et al. |
| 11,200,328 B2 | 12/2021 | Shpurov et al. |
| 11,200,411 B2 | 12/2021 | Rizvi et al. |
| 11,210,857 B2 | 12/2021 | Rizvi et al. |
| 11,222,286 B2 | 1/2022 | Choe et al. |
| 11,232,304 B2 | 1/2022 | Navarro et al. |
| 11,243,787 B2 | 2/2022 | Myers |
| 11,276,257 B2 | 3/2022 | Moghtadai et al. |
| 11,303,642 B2 | 4/2022 | Dunjic et al. |
| 11,334,574 B2 | 5/2022 | Caputo et al. |
| 11,347,744 B2 | 5/2022 | Tseretopoulos et al. |
| 11,349,871 B2 | 5/2022 | Moon et al. |
| 11,354,442 B2 | 6/2022 | Haldenby et al. |
| 11,361,566 B2 | 6/2022 | Collinson et al. |
| 11,373,229 B2 | 6/2022 | Tseretopoulos et al. |
| 11,392,776 B2 | 7/2022 | Lozon et al. |
| 11,393,020 B2 | 7/2022 | Mathew et al. |
| 11,394,668 B1 | 7/2022 | Subbunarayanan et al. |
| 11,397,765 B2 | 7/2022 | Volkovs et al. |
| 11,409,811 B2 | 8/2022 | D'Agostino |
| 11,411,734 B2 | 8/2022 | Shpurov et al. |
| 11,430,242 B2 | 8/2022 | Moghtadai |
| 11,436,809 B2 | 9/2022 | Rizvi et al. |
| 11,451,669 B1 | 9/2022 | Navarro et al. |
| 11,469,878 B2 | 10/2022 | Shpurov et al. |
| 11,470,091 B2 | 10/2022 | McCarter et al. |
| 11,470,143 B2 | 10/2022 | Joheb et al. |
| 11,475,059 B2 | 10/2022 | Liu et al. |
| 11,475,251 B2 | 10/2022 | Morin et al. |
| 11,477,265 B2 | 10/2022 | McPhee et al. |
| 11,507,622 B2 | 11/2022 | Grebenisan et al. |
| 11,507,868 B2 | 11/2022 | Kwong et al. |
| 11,546,345 B2 | 1/2023 | D'Agostino et al. |
| 11,580,762 B2 | 2/2023 | Rizvi et al. |
| 11,600,064 B2 | 3/2023 | Navarro et al. |
| 11,604,899 B2 | 3/2023 | Haldenby et al. |
| 11,620,741 B2 | 4/2023 | Kuruvilla et al. |
| 11,632,311 B2 | 4/2023 | Miller et al. |
| 11,651,100 B2 | 5/2023 | Dunjic et al. |
| 11,663,488 B2 | 5/2023 | Volkovs et al. |
| 11,671,536 B2 | 6/2023 | Navarro et al. |
| 11,687,995 B2 | 6/2023 | Tseretopoulos et al. |
| 11,689,484 B2 | 6/2023 | Moon et al. |
| 11,704,782 B2 | 7/2023 | Wakim et al. |
| 11,741,305 B2 | 8/2023 | Skaljin et al. |
| 11,743,210 B2 | 8/2023 | Moon et al. |
| 11,748,400 B2 | 9/2023 | Volkovs et al. |
| 11,756,388 B2 | 9/2023 | Pratten et al. |
| 11,777,918 B2 | 10/2023 | Moon et al. |
| 11,782,935 B2 | 10/2023 | Caputo et al. |
| 11,789,909 B2 | 10/2023 | Grebenisan et al. |
| 11,790,012 B2 | 10/2023 | D'Agostino |
| 11,790,354 B2 | 10/2023 | Gandhi et al. |
| 11,797,962 B2 | 10/2023 | Jones et al. |
| 11,809,486 B2 | 11/2023 | Liu et al. |
| 11,809,577 B2 | 11/2023 | Begg et al. |
| 11,811,826 B2 | 11/2023 | Moon et al. |
| 11,842,252 B2 | 12/2023 | Kuang et al. |
| 11,875,398 B2 | 1/2024 | Pratten et al. |
| 11,880,811 B2 | 1/2024 | Pawelkiewicz et al. |
| 11,886,764 B2 | 1/2024 | Lam |
| 11,928,112 B2 | 3/2024 | Dunjic et al. |
| 11,941,525 B2 | 3/2024 | Morin et al. |
| 11,941,703 B2 | 3/2024 | Kuruvilla et al. |
| 11,955,117 B2 | 4/2024 | McDermid et al. |
| 11,966,491 B2 | 4/2024 | D'Agostino |
| 11,978,085 B2 | 5/2024 | Rai et al. |
| 11,978,090 B2 | 5/2024 | Navarro et al. |
| 11,985,153 B2 | 5/2024 | Karl |
| 11,995,121 B2 | 5/2024 | Volkovs et al. |
| 12,008,315 B2 | 6/2024 | Miller et al. |
| 12,014,303 B2 | 6/2024 | Carvalho et al. |
| 12,019,594 B2 | 6/2024 | Floyd et al. |
| 12,021,874 B2 | 6/2024 | Dunjic et al. |
| 12,039,535 B2 | 7/2024 | Dunjic et al. |
| 12,052,363 B2 | 7/2024 | Shpurov et al. |
| 12,061,652 B2 | 8/2024 | Miller et al. |
| 12,067,130 B2 | 8/2024 | Shpurov et al. |
| 12,067,580 B2 | 8/2024 | Jeske et al. |
| 12,079,351 B2 | 9/2024 | Begg et al. |
| 12,106,220 B2 | 10/2024 | Volkovs et al. |
| 12,111,793 B2 | 10/2024 | Grebenisan et al. |
| 12,124,925 B2 | 10/2024 | Rho et al. |
| 12,136,079 B2 | 11/2024 | Jones et al. |
| 12,164,542 B1 | 12/2024 | Rahman et al. |
| 12,169,693 B2 | 12/2024 | Lu |
| 12,182,800 B2 | 12/2024 | Navarro et al. |
| 12,198,109 B2 | 1/2025 | Abbas |
| 12,198,510 B2 | 1/2025 | Pratten et al. |
| 12,210,534 B2 | 1/2025 | Cashion et al. |
| 12,211,274 B2 | 1/2025 | Ma et al. |
| 12,217,011 B2 | 2/2025 | Luo et al. |
| 12,223,549 B2 | 2/2025 | Bouëttée al. |
| 12,229,690 B2 | 2/2025 | Stanevich et al. |
| 12,254,512 B2 | 3/2025 | Heglin et al. |
| 12,282,785 B2 | 4/2025 | Karbasi et al. |
| 12,288,236 B2 | 4/2025 | Volkovs et al. |
| 12,299,149 B2 | 5/2025 | Nikoghossian et al. |
| 12,316,715 B2 | 5/2025 | Taheri et al. |
| 12,321,861 B2 | 6/2025 | Volkovs et al. |
| 12,326,856 B2 | 6/2025 | Mohammed et al. |
| 12,333,354 B2 | 6/2025 | Mohammed et al. |
| 12,353,969 B2 | 7/2025 | Kuang et al. |
| 12,354,094 B2 | 7/2025 | Jones et al. |
| 12,373,795 B2 | 7/2025 | Misler et al. |
| 2007/0255658 A1* | 11/2007 | Grad .................... G06Q 40/02 |
| | | 705/42 |
| 2014/0067634 A1 | 3/2014 | Sowder et al. |
| 2017/0032459 A1 | 2/2017 | Kaminski et al. |
| 2018/0268818 A1 | 9/2018 | Schoenmackers et al. |
| 2019/0172045 A1 | 6/2019 | Dunjic et al. |
| 2020/0058068 A1 | 2/2020 | Gandhi et al. |
| 2021/0027160 A1 | 1/2021 | Volkovs et al. |
| 2021/0037040 A1 | 2/2021 | Aleks et al. |
| 2021/0117893 A1 | 4/2021 | Sohum et al. |
| 2021/0232950 A1 | 7/2021 | Kono |
| 2021/0264461 A1 | 8/2021 | Fam |
| 2021/0303973 A1 | 9/2021 | Edwards et al. |
| 2021/0407016 A1 | 12/2021 | Kuruvilla et al. |
| 2022/0058489 A1 | 2/2022 | Volkovs et al. |
| 2022/0108069 A1 | 4/2022 | Lee |
| 2022/0156095 A1 | 5/2022 | Myers |
| 2022/0157094 A1 | 5/2022 | Moghtadai et al. |
| 2022/0172083 A1 | 6/2022 | Wu et al. |
| 2022/0188705 A1 | 6/2022 | Davoodi et al. |
| 2022/0198411 A1 | 6/2022 | Jones et al. |

(56) References Cited

U.S. PATENT DOCUMENTS

| | | | |
|---|---|---|---|
| 2022/0198432 A1 | 6/2022 | Jones et al. | |
| 2022/0198445 A1 | 6/2022 | Jones et al. | |
| 2022/0207295 A1 | 6/2022 | Stanevich et al. | |
| 2022/0207430 A1 | 6/2022 | Dickie et al. | |
| 2022/0207432 A1 | 6/2022 | Whelan et al. | |
| 2022/0207606 A1 | 6/2022 | Dickie et al. | |
| 2022/0245060 A1 | 8/2022 | Kathuria et al. | |
| 2022/0261885 A1 | 8/2022 | Kim et al. | |
| 2022/0270155 A1 | 8/2022 | Volkovs et al. | |
| 2022/0277213 A1 | 9/2022 | Braviner et al. | |
| 2022/0277227 A1 | 9/2022 | Yu et al. | |
| 2022/0277323 A1 | 9/2022 | Whelan et al. | |
| 2022/0284450 A1 | 9/2022 | Asta et al. | |
| 2022/0300903 A1 | 9/2022 | Huang et al. | |
| 2022/0309573 A1 | 9/2022 | Mathew et al. | |
| 2022/0318573 A1 | 10/2022 | Smith et al. | |
| 2022/0318617 A1 | 10/2022 | Wong et al. | |
| 2022/0327397 A1 | 10/2022 | Braviner et al. | |
| 2022/0327430 A1 | 10/2022 | Zuberi et al. | |
| 2022/0327431 A1 | 10/2022 | Braviner et al. | |
| 2022/0327432 A1 | 10/2022 | Gutierrez Bugarin et al. | |
| 2022/0327625 A1 | 10/2022 | Leung et al. | |
| 2022/0335718 A1 | 10/2022 | Ma et al. | |
| 2022/0343422 A1 | 10/2022 | Zuberi et al. | |
| 2022/0366064 A1 | 11/2022 | Nikoghossian et al. | |
| 2022/0383301 A1 | 12/2022 | Jones et al. | |
| 2022/0383313 A1 | 12/2022 | Jones et al. | |
| 2022/0383314 A1 | 12/2022 | Jones et al. | |
| 2022/0405299 A1 | 12/2022 | Leung et al. | |
| 2022/0414495 A1 | 12/2022 | Stanevich et al. | |
| 2022/0415022 A1* | 12/2022 | Brumby | G06V 10/22 |
| 2023/0006809 A1 | 1/2023 | Shpurov et al. | |
| 2023/0007075 A1 | 1/2023 | Mcphee et al. | |
| 2023/0011451 A1 | 1/2023 | Lu | |
| 2023/0048437 A1 | 2/2023 | Karbasi et al. | |
| 2023/0083899 A1 | 3/2023 | Gandouet et al. | |
| 2023/0086653 A1 | 3/2023 | Zykh et al. | |
| 2023/0107703 A1 | 4/2023 | Zhang et al. | |
| 2023/0113752 A1 | 4/2023 | Jorlett et al. | |
| 2023/0119108 A1 | 4/2023 | Volkovs et al. | |
| 2023/0131935 A1 | 4/2023 | Volkovs et al. | |
| 2023/0153461 A1 | 5/2023 | Kalra et al. | |
| 2023/0195734 A1 | 6/2023 | Cashion et al. | |
| 2023/0196406 A1 | 6/2023 | Gandouet et al. | |
| 2023/0206320 A1 | 6/2023 | Guan | |
| 2023/0244917 A1 | 8/2023 | Loaiza Ganem et al. | |
| 2023/0244962 A1 | 8/2023 | Volkovs et al. | |
| 2023/0252301 A1 | 8/2023 | Volkovs et al. | |
| 2023/0259883 A1 | 8/2023 | Misler et al. | |
| 2023/0267367 A1 | 8/2023 | Volkovs et al. | |
| 2023/0267475 A1 | 8/2023 | Navarro et al. | |
| 2023/0306434 A1 | 9/2023 | Dunjic et al. | |
| 2023/0316485 A1 | 10/2023 | Wakim et al. | |
| 2023/0318994 A1 | 10/2023 | Moon et al. | |
| 2023/0336615 A1 | 10/2023 | Joheb et al. | |
| 2023/0342481 A1 | 10/2023 | Nikoghossian et al. | |
| 2023/0344814 A1 | 10/2023 | Moon et al. | |
| 2023/0351116 A1 | 11/2023 | Skaljin et al. | |
| 2023/0368048 A1 | 11/2023 | Yang et al. | |
| 2023/0377047 A1 | 11/2023 | Bouëttéet al. | |
| 2023/0385693 A1 | 11/2023 | Cresswell et al. | |
| 2023/0385694 A1 | 11/2023 | Cresswell et al. | |
| 2023/0386190 A1 | 11/2023 | Cresswell et al. | |
| 2023/0394452 A1 | 12/2023 | Jones et al. | |
| 2023/0401192 A1 | 12/2023 | Yang et al. | |
| 2023/0401553 A1 | 12/2023 | Navarro et al. | |
| 2023/0401572 A1 | 12/2023 | Navarro et al. | |
| 2023/0419302 A1 | 12/2023 | Navarro et al. | |
| 2023/0419402 A1 | 12/2023 | Ghelichi et al. | |
| 2024/0020534 A1 | 1/2024 | Perez Vallejo et al. | |
| 2024/0062117 A1 | 2/2024 | Kuang et al. | |
| 2024/0106851 A1 | 3/2024 | Kennedy et al. | |
| 2024/0119346 A1 | 4/2024 | Chang et al. | |
| 2024/0126575 A1 | 4/2024 | Kiriakou et al. | |
| 2024/0127036 A1 | 4/2024 | Zuberi et al. | |
| 2024/0127214 A1 | 4/2024 | Wander et al. | |
| 2024/0193562 A1 | 6/2024 | Pratten et al. | |
| 2024/0202756 A1 | 6/2024 | Karl et al. | |
| 2024/0203405 A1 | 6/2024 | McDermid et al. | |
| 2024/0211732 A1 | 6/2024 | Wander et al. | |
| 2024/0212049 A1 | 6/2024 | Ghelichi et al. | |
| 2024/0220653 A1 | 7/2024 | D'Agostino | |
| 2024/0232614 A1 | 7/2024 | Esmaeili et al. | |
| 2024/0232950 A1 | 7/2024 | Navarro et al. | |
| 2024/0249310 A1 | 7/2024 | Rai et al. | |
| 2024/0256903 A1 | 8/2024 | Ens et al. | |
| 2024/0256904 A1 | 8/2024 | Leung et al. | |
| 2024/0256968 A1 | 8/2024 | Hosseinzadeh et al. | |
| 2024/0264723 A1* | 8/2024 | Davidson | G06N 3/045 |
| 2024/0265055 A1 | 8/2024 | Purkayastha | |
| 2024/0281467 A1 | 8/2024 | Volkovs et al. | |
| 2024/0281808 A1 | 8/2024 | Vouitsis et al. | |
| 2024/0281818 A1 | 8/2024 | Golestan Irani et al. | |
| 2024/0289645 A1 | 8/2024 | Makhijani et al. | |
| 2024/0289876 A1 | 8/2024 | Mathew et al. | |
| 2024/0303551 A1 | 9/2024 | Li et al. | |
| 2024/0304182 A1 | 9/2024 | Hamilton et al. | |
| 2024/0330772 A1 | 10/2024 | Cresswell et al. | |
| 2024/0330809 A1 | 10/2024 | Carvalho et al. | |
| 2024/0338520 A1 | 10/2024 | Misler et al. | |
| 2024/0346338 A1 | 10/2024 | Desai et al. | |
| 2024/0370880 A1 | 11/2024 | Jeske et al. | |
| 2024/0370881 A1 | 11/2024 | Jeske et al. | |
| 2024/0385838 A1 | 11/2024 | Yu et al. | |
| 2024/0386295 A1 | 11/2024 | Yu et al. | |
| 2024/0386325 A1 | 11/2024 | Yu et al. | |
| 2024/0386326 A1 | 11/2024 | Yu et al. | |
| 2024/0386427 A1 | 11/2024 | Abbas et al. | |
| 2024/0394569 A1 | 11/2024 | Farhadi Hassan Kiadeh et al. | |
| 2024/0394588 A1 | 11/2024 | Heglan et al. | |
| 2024/0403702 A1 | 12/2024 | Deljavan Farshi | |
| 2024/0403862 A1 | 12/2024 | Abbas et al. | |
| 2024/0412069 A1 | 12/2024 | Volkovs et al. | |
| 2024/0412078 A1 | 12/2024 | Ghelichi et al. | |
| 2024/0412083 A1 | 12/2024 | Starszyk et al. | |
| 2024/0419978 A1 | 12/2024 | Stein et al. | |
| 2024/0420010 A1 | 12/2024 | Cirulis et al. | |
| 2024/0420011 A1 | 12/2024 | Cirulis et al. | |
| 2024/0428283 A1 | 12/2024 | Belbahri et al. | |
| 2025/0013363 A1 | 1/2025 | Estoesta et al. | |
| 2025/0013697 A1 | 1/2025 | Estoesta et al. | |
| 2025/0013927 A1 | 1/2025 | Rho et al. | |
| 2025/0014010 A1 | 1/2025 | Jones et al. | |
| 2025/0014052 A1 | 1/2025 | Bhattacharjee et al. | |
| 2025/0028852 A1 | 1/2025 | Chowanski et al. | |
| 2025/0028934 A1 | 1/2025 | Wong et al. | |
| 2025/0029012 A1 | 1/2025 | Rho et al. | |
| 2025/0045601 A1 | 2/2025 | Zuberi et al. | |
| 2025/0053387 A1 | 2/2025 | Wang et al. | |
| 2025/0068646 A1 | 2/2025 | Rahman et al. | |
| 2025/0068853 A1 | 2/2025 | Lu | |
| 2025/0069063 A1 | 2/2025 | Navarro et al. | |
| 2025/0077187 A1 | 3/2025 | Guttridge et al. | |
| 2025/0077188 A1 | 3/2025 | Guttridge et al. | |
| 2025/0077189 A1 | 3/2025 | Guttridge et al. | |
| 2025/0077190 A1 | 3/2025 | Guttridge et al. | |
| 2025/0077204 A1 | 3/2025 | Guttridge et al. | |
| 2025/0077227 A1 | 3/2025 | Guttridge et al. | |
| 2025/0077396 A1 | 3/2025 | Sen | |
| 2025/0077397 A1 | 3/2025 | Sen | |
| 2025/0077399 A1 | 3/2025 | Sen | |
| 2025/0077400 A1 | 3/2025 | Sen | |
| 2025/0077556 A1 | 3/2025 | Guttridge et al. | |
| 2025/0077681 A1 | 3/2025 | Sen | |
| 2025/0077682 A1 | 3/2025 | Guttridge et al. | |
| 2025/0077939 A1 | 3/2025 | Tabatabaei et al. | |
| 2025/0078324 A1 | 3/2025 | Gormley | |
| 2025/0078325 A1 | 3/2025 | Gormley | |
| 2025/0078344 A1 | 3/2025 | Gormley | |
| 2025/0078345 A1 | 3/2025 | Gormley | |
| 2025/0078972 A1 | 3/2025 | Gormley | |
| 2025/0085936 A1 | 3/2025 | Guttridge et al. | |
| 2025/0086096 A1 | 3/2025 | Guttridge et al. | |
| 2025/0086440 A1 | 3/2025 | Erb et al. | |

(56) References Cited

U.S. PATENT DOCUMENTS

| | | | |
|---|---|---|---|
| 2025/0086441 | A1 | 3/2025 | Guttridge et al. |
| 2025/0086451 | A1 | 3/2025 | Guttridge et al. |
| 2025/0086551 | A1 | 3/2025 | Zhao |
| 2025/0094437 | A1 | 3/2025 | Upendran |
| 2025/0103609 | A1 | 3/2025 | Upendran |
| 2025/0103961 | A1 | 3/2025 | Cresswell et al. |
| 2025/0103980 | A1 | 3/2025 | Deljavan Farshi et al. |
| 2025/0104024 | A1 | 3/2025 | Abbas |
| 2025/0104029 | A1 | 3/2025 | Deljavan Farshi et al. |
| 2025/0104047 | A1 | 3/2025 | Mashkevich |
| 2025/0104050 | A1 | 3/2025 | Mashkevich |
| 2025/0104059 | A1 | 3/2025 | Mashkevich |
| 2025/0104074 | A1 | 3/2025 | Tsang et al. |
| 2025/0104306 | A1 | 3/2025 | Mashkevich |
| 2025/0104700 | A1 | 3/2025 | Henault-Ethier et al. |
| 2025/0106060 | A1 | 3/2025 | Gormley et al. |
| 2025/0106201 | A1 | 3/2025 | Gormley |
| 2025/0110805 | A1 | 4/2025 | Starszyk et al. |
| 2025/0117411 | A1 | 4/2025 | Mohammed |
| 2025/0117595 | A1 | 4/2025 | Taheri |
| 2025/0117596 | A1 | 4/2025 | Taheri |
| 2025/0117623 | A1 | 4/2025 | Devarajan et al. |
| 2025/0117629 | A1 | 4/2025 | Pandey et al. |
| 2025/0117630 | A1 | 4/2025 | Taheri |
| 2025/0117769 | A1 | 4/2025 | Taheri |
| 2025/0117836 | A1 | 4/2025 | Taheri et al. |
| 2025/0117853 | A1 | 4/2025 | Pandey et al. |
| 2025/0117854 | A1 | 4/2025 | Pandey et al. |
| 2025/0117855 | A1 | 4/2025 | Pandey et al. |
| 2025/0117856 | A1 | 4/2025 | Pandey et al. |
| 2025/0119396 | A1 | 4/2025 | Taheri |
| 2025/0119494 | A1 | 4/2025 | Pandey et al. |
| 2025/0119495 | A1 | 4/2025 | Pandey et al. |
| 2025/0124039 | A1 | 4/2025 | Cashion et al. |
| 2025/0124240 | A1 | 4/2025 | Luo et al. |
| 2025/0131718 | A1 | 4/2025 | Ma et al. |
| 2025/0138838 | A1 | 5/2025 | Ramesh et al. |
| 2025/0139267 | A1 | 5/2025 | Zykh et al. |
| 2025/0139382 | A1 | 5/2025 | Mohammed et al. |
| 2025/0139708 | A1 | 5/2025 | Bouëttéet al. |
| 2025/0147733 | A1 | 5/2025 | Abbas et al. |
| 2025/0148321 | A1 | 5/2025 | Stanevich et al. |
| 2025/0165375 | A1 | 5/2025 | Cresswell et al. |
| 2025/0165866 | A1 | 5/2025 | Cresswell et al. |
| 2025/0173170 | A1 | 5/2025 | Glynn-Udrow et al. |
| 2025/0173568 | A1 | 5/2025 | Cresswell et al. |
| 2025/0173618 | A1 | 5/2025 | Cresswell et al. |
| 2025/0173619 | A1 | 5/2025 | Cresswell et al. |
| 2025/0173725 | A1 | 5/2025 | Devarajan et al. |
| 2025/0181321 | A1 | 6/2025 | Gormley |
| 2025/0182028 | A1 | 6/2025 | Gormley |
| 2025/0182196 | A1 | 6/2025 | Gormley |
| 2025/0182222 | A1 | 6/2025 | Gormley |
| 2025/0191062 | A1 | 6/2025 | Heglin et al. |
| 2025/0217175 | A1 | 7/2025 | Karbasi et al. |
| 2025/0225560 | A1 | 7/2025 | Bajaj et al. |
| 2025/0231668 | A1 | 7/2025 | Tao et al. |
| 2025/0231750 | A1 | 7/2025 | Lim et al. |
| 2025/0231774 | A1 | 7/2025 | Tao et al. |
| 2025/0231775 | A1 | 7/2025 | Tao et al. |
| 2025/0231793 | A1 | 7/2025 | Lim et al. |
| 2025/0232130 | A1 | 7/2025 | Tao et al. |
| 2025/0232351 | A1 | 7/2025 | Tao et al. |
| 2025/0232375 | A1 | 7/2025 | Tao et al. |
| 2025/0232376 | A1 | 7/2025 | Tao et al. |
| 2025/0232377 | A1 | 7/2025 | Tao et al. |
| 2025/0232503 | A1 | 7/2025 | Lim et al. |
| 2025/0238536 | A1 | 7/2025 | Nikoghossian et al. |
| 2025/0245071 | A1 | 7/2025 | Ionescu et al. |
| 2025/0245511 | A1 | 7/2025 | D'Agostino et al. |

OTHER PUBLICATIONS

Heglin et al., "Auto-Adjudication Process Via Machine Learning," U.S. Appl. No. 19/053,942, filed Feb. 14, 2025.

* cited by examiner

Figure 1B:
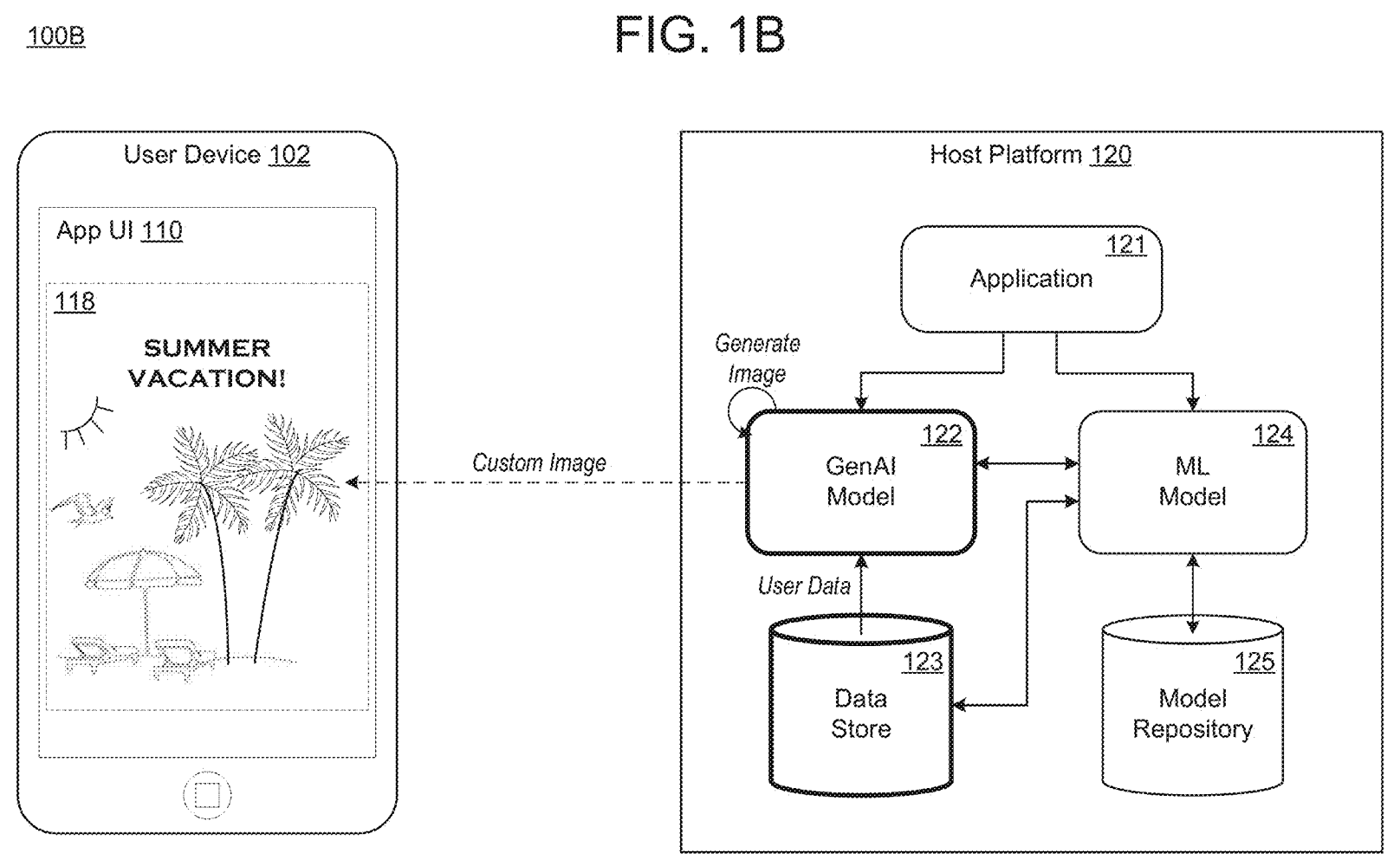

Host Platform 120

Application 121

ML Model 124

Model Repository 125

GenAI Model 122

Generate Image

Data Store 123

User Data

Custom Image

User Device 102

App UI 110

118

SUMMER VACATION!

Figure 4:
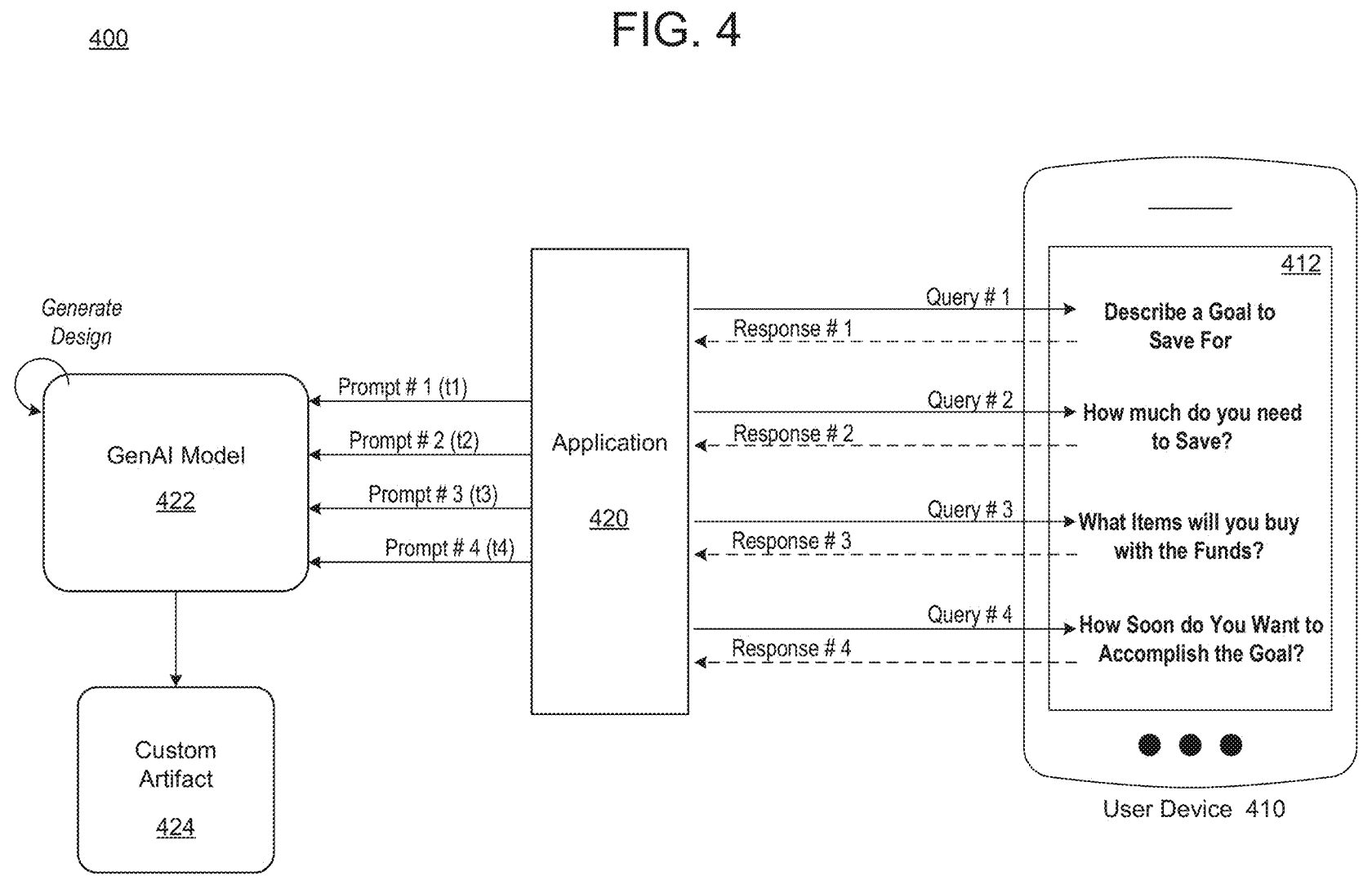

User Device 410

412

Describe a Goal to Save For

How much do you need to Save?

What Items will you buy with the Funds?

How Soon do You Want to Accomplish the Goal?

Query # 1
Query # 2
Query # 3
Query # 4

Response # 1
Response # 2
Response # 3
Response # 4

Application

420

Prompt # 1 (t1)
Prompt # 2 (t2)
Prompt # 3 (t3)
Prompt # 4 (t4)

Generate Design

GenAI Model

422

Custom Artifact

User Interface 631

Possible Goals:

Buying a New House
632

Yes    No
633

Kids New Car
634

Yes    No
635

GenAI Model
623

800                    FIG. 8
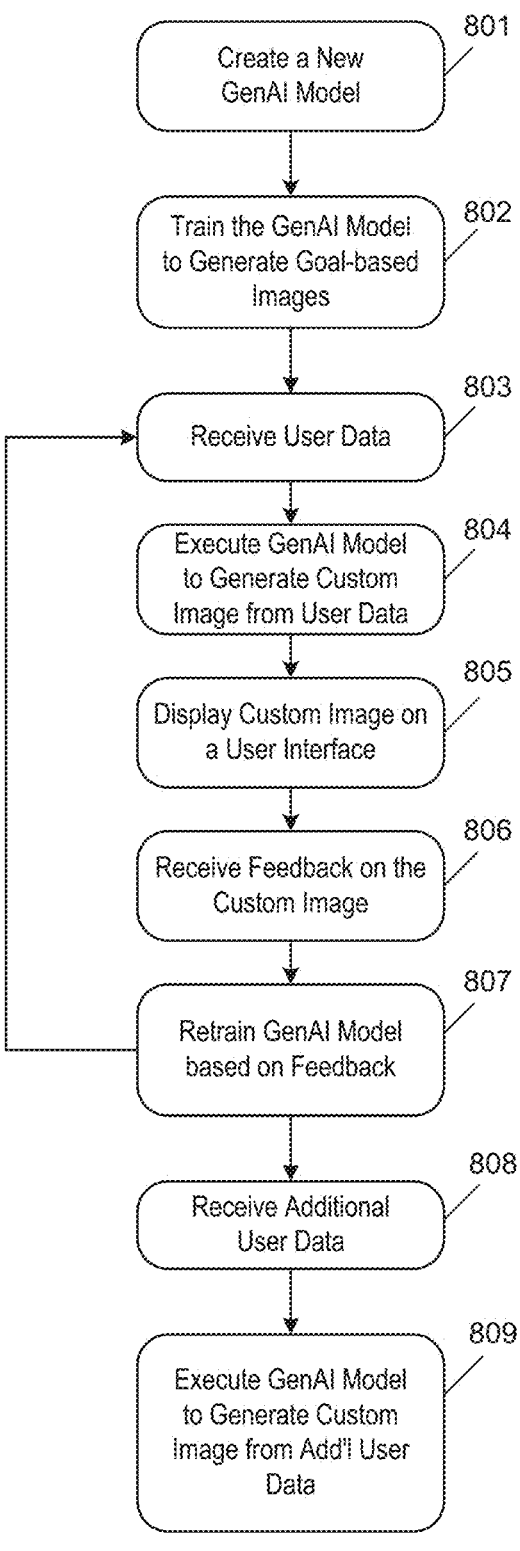

900

901
Storing a GenAI Model

902
Displaying Prompts on a UI

903
Receiving an Identifier of a Goal and Attributes of the Goal based on the Prompts 904
Executing the GenAI Model on the Goal and the Attributes to Generate a Custom Image of the Goal 905
Displaying the Custom Image 910                    FIG. 9B
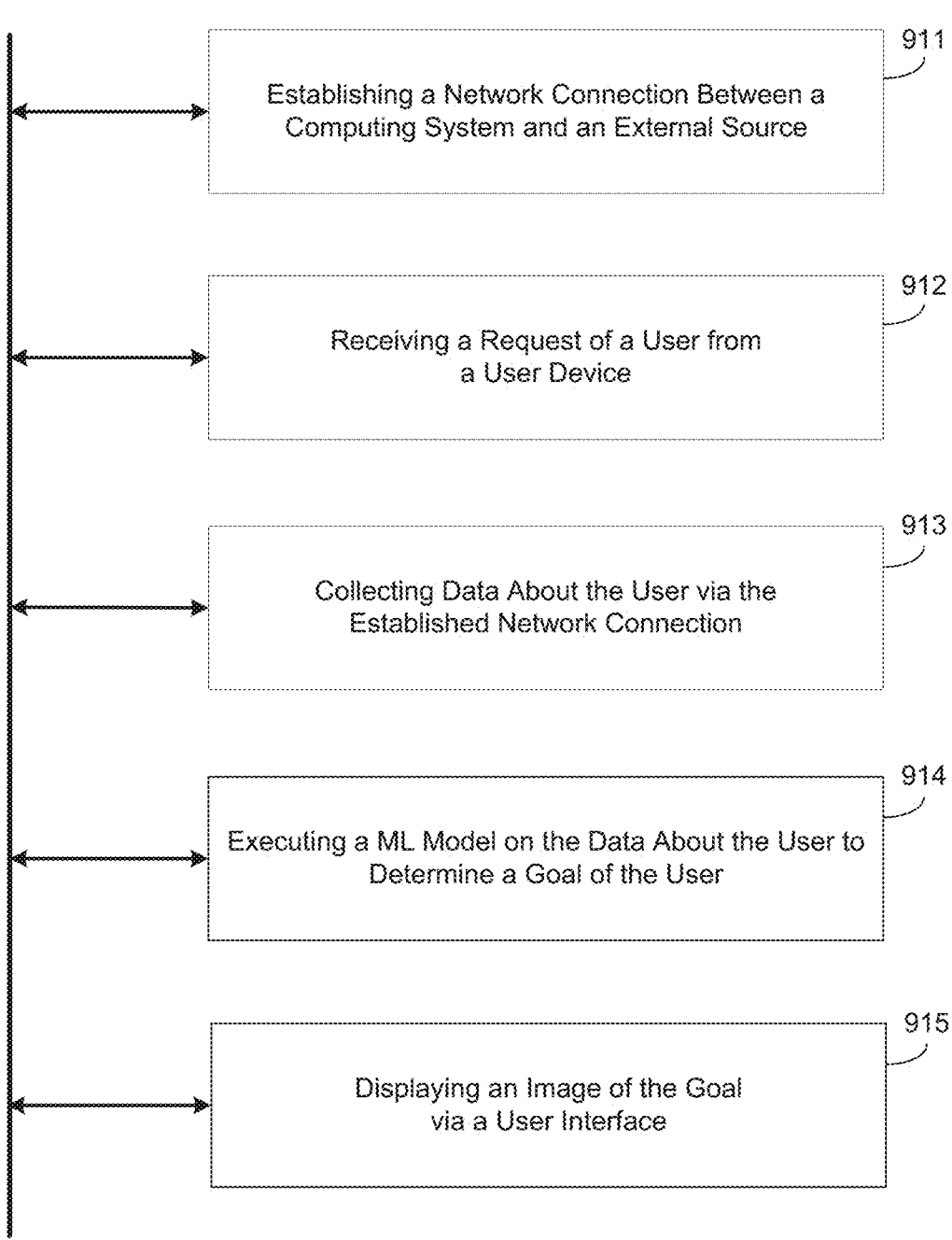
911
Establishing a Network Connection Between a
Computing System and an External Source
912
Receiving a Request of a User from
a User Device
913
Collecting Data About the User via the
Established Network Connection
914
Executing a ML Model on the Data About the User to
Determine a Goal of the User
915
Displaying an Image of the Goal
via a User Interface 920	FIG. 9C
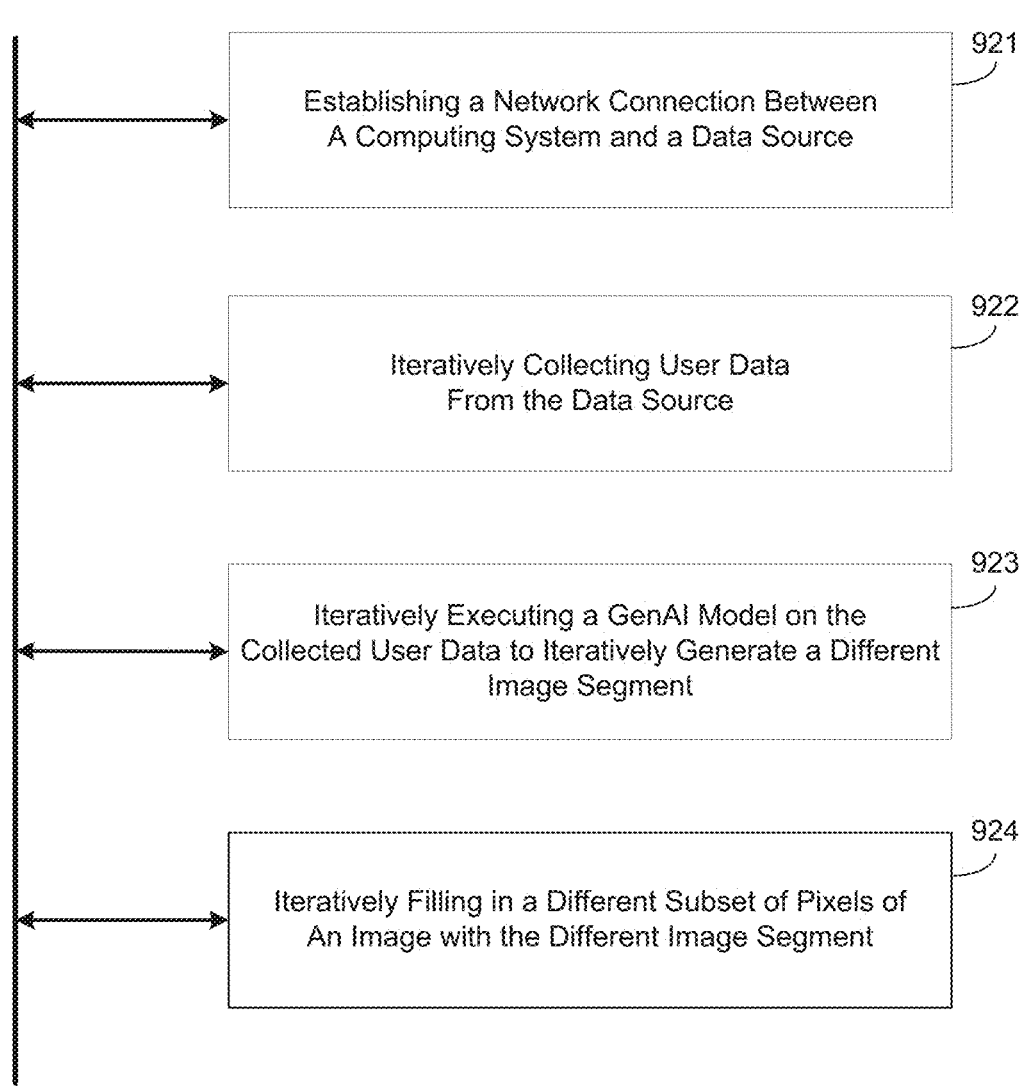
921
Establishing a Network Connection Between
A Computing System and a Data Source
922
Iteratively Collecting User Data
From the Data Source
923
Iteratively Executing a GenAI Model on the
Collected User Data to Iteratively Generate a Different
Image Segment
924
Iteratively Filling in a Different Subset of Pixels of
An Image with the Different Image Segment

930                          FIG. 9D

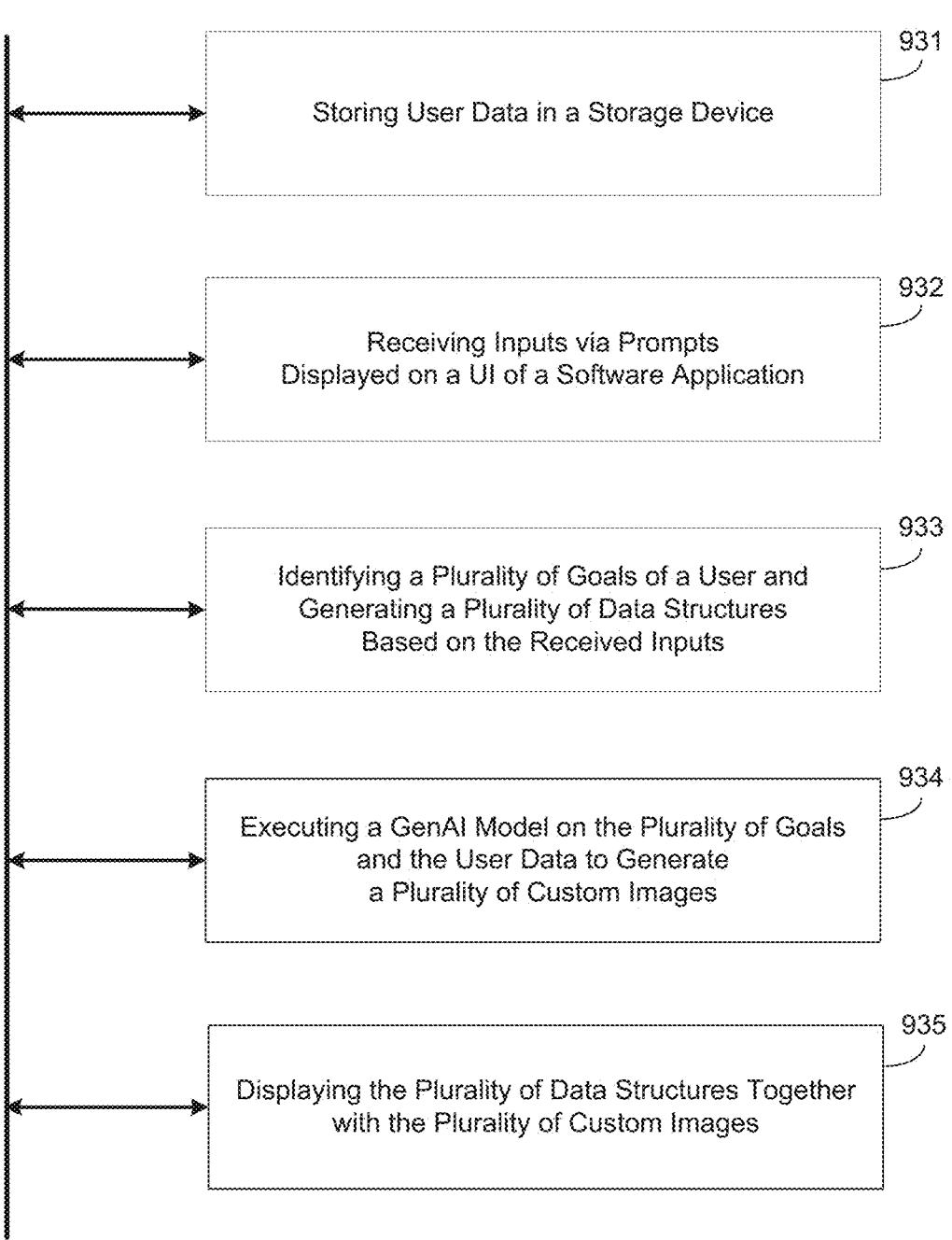

931

Storing User Data in a Storage Device

932

Receiving Inputs via Prompts
Displayed on a UI of a Software Application

933

Identifying a Plurality of Goals of a User and
Generating a Plurality of Data Structures
Based on the Received Inputs

934

Executing a GenAI Model on the Plurality of Goals
and the User Data to Generate
a Plurality of Custom Images

935

Displaying the Plurality of Data Structures Together
with the Plurality of Custom Images

940

941

Training a GenAI Model to Generate Images

942

Executing the GenAI Model on Input Data to Generate a Custom Image Corresponding to the Input Data, and Displaying the Custom Image

943

Receiving Feedback About the Custom Image via a User Interface

944

Retraining the GenAI Model based on the Custom Image and the Received Feedback

1000

PROMPT ENGINEERING AND GENERATIVE AI FOR GOAL-BASED IMAGERY

BACKGROUND

Research has shown that as people approach a goal, such as a financial goal, a personal goal, an educational goal, etc., that person's pursuit of the goal is likely to increase. Specifically, as the goal becomes more of a reality (e.g., gets closer in time to occurring, etc.), people tend to visualize the goal easier than other goals farther away. As such, people tend to increase their efforts toward accomplishing the most visible/nearest goal while leaving other goals for later. Meanwhile, prompt engineering is the art and science of using machine learning to generate output based on prompts.

SUMMARY

One example embodiment provides an apparatus that may include a memory configured to store a generative artificial intelligence (GenAI) model configured to create images; and a processor configured to display a plurality of prompts on a user interface of a software application, receive an identifier of a goal of the user and attributes of the goal via the plurality of prompts on the user interface, execute the GenAI model on the identifier of the goal of the user and the attributes of the goal to generate a custom image of the goal for the user, and display the custom image of the goal via the user interface of the software application.

Another example embodiment provides a method that includes one or more of storing a generative artificial intelligence (GenAI) model configured to create images, displaying a plurality of prompts on a user interface of a software application, receiving an identifier of a goal of the user and attributes of the goal via the plurality of prompts on the user interface, executing the GenAI model on the identifier of the goal of the user and the attributes of the goal to generate a custom image of the goal for the user, and displaying the custom image of the goal via the user interface of the software application.

A further example embodiment provides a computer-readable medium comprising instructions, that when read by a processor, cause the processor to perform one or more of storing a generative artificial intelligence (GenAI) model configured to create images, displaying a plurality of prompts on a user interface of a software application, receiving an identifier of a goal of the user and attributes of the goal via the plurality of prompts on the user interface, executing the GenAI model on the identifier of the goal of the user and the attributes of the goal to generate a custom image of the goal for the user, and displaying the custom image of the goal via the user interface of the software application.

A further example embodiment provides an apparatus that may include a network interface configured to establish a network connection between the computing system and one or more external sources over a computer network, and a processor configured to receive a request from a user via a software application on a user device, collect data about the user from the one or more external sources via the established network connection, execute a machine learning model on the collected data about the user to determine a goal of the user, and display an image of the goal via a user interface of the software application.

A further example embodiment provides a method that includes one or more of establishing a network connection between a computing system and one or more external sources over a computer network, receiving a request from a user via a software application on a user device, collecting data about the user from the one or more external sources via the established network connection, executing a machine learning model on the collected data about the user to determine a goal of the user, and displaying an image of the goal via a user interface of the software application.

A further example embodiment provides a computer-readable medium comprising instructions, that when read by a processor, cause the processor to perform one or more of establishing a network connection between a computing system and one or more external sources over a computer network, receiving a request from a user via a software application on a user device, collecting data about the user from the one or more external sources via the established network connection, executing a machine learning model on the collected data about the user to determine a goal of the user, and displaying an image of the goal via a user interface of the software application.

A further example embodiment provides an apparatus that may include a network interface that establishes a network connection between the computing system and a data source, and a processor that iteratively executes a sequence of steps that comprise collecting user data from the data source, executing a generative artificial intelligence (GenAI) model on the collected user data to generate a different image segment, and filling in a different subset of pixels of an image with the generated image segment and displaying the partially-filled in image on a user interface.

A further example embodiment provides a method that includes one or more of establishing a network connection between the computing system and a data source, iteratively performing a sequence of steps comprising, collecting user data from the data source, executing a generative artificial intelligence (GenAI) model on the collected user data to generate a different image segment, and filling in a different subset of pixels of an image with the generated image segment and display the partially-filled in image on a user interface.

A further example embodiment provides a computer-readable medium comprising instructions, that when read by a processor, cause the processor to perform one or more of establishing a network connection between the computing system and a data source, iteratively performing a sequence of steps comprising, collecting user data from the data source, executing a generative artificial intelligence (GenAI) model on the collected user data to generate a different image segment, and filling in a different subset of pixels of an image with the generated image segment and display the partially-filled in image on a user interface.

A further example embodiment provides an apparatus that may include a storage configured to store user data, and a processor configured to receive inputs via a prompts displayed on a user interface of a software application, identify a plurality of goals within the received inputs and generate a plurality of data structures corresponding to the plurality of goals, respectively, execute a generative artificial intelligence (GenAI) model on the plurality of goals and the stored user data to generate a plurality of custom images of the plurality of goals, and display a plurality of identifiers of the plurality of data structures corresponding to the plurality of goals on a user interface, and simultaneously display the plurality of custom images next to the plurality goals, respectively.

A further example embodiment provides a method that includes one or more of storing user data in a storage device, receiving inputs via prompts displayed on a user interface of a software application, identifying a plurality of goals within the received inputs and generating a plurality of data structures corresponding to the plurality of goals, respectively, executing a generative artificial intelligence (GenAI) model on the plurality of goals and the stored user data to generate a plurality of custom images of the plurality of goals, and displaying a plurality of identifiers of the plurality of data structures corresponding to the plurality of goals on a user interface, and simultaneously display the plurality of custom images next to the plurality goals, respectively.

A further example embodiment provides a computer-readable medium comprising instructions, that when read by a processor, cause the processor to perform one or more of storing user data in a storage device, receiving inputs via prompts displayed on a user interface of a software application, identifying a plurality of goals within the received inputs and generating a plurality of data structures corresponding to the plurality of goals, respectively, executing a generative artificial intelligence (GenAI) model on the plurality of goals and the stored user data to generate a plurality of custom images of the plurality of goals, and displaying a plurality of identifiers of the plurality of data structures corresponding to the plurality of goals on a user interface, and simultaneously display the plurality of custom images next to the plurality goals, respectively.

A further example embodiment provides an apparatus that may include a processor configured to train a generative artificial intelligence (GenAI) model to generate images based on user data using a dataset of images, execute the GenAI model based on input data from a user interface of a software application to generate an image corresponding to the input data, and display the image via a user interface of a software application, receive feedback about the image via the user interface, and retrain the GenAI model based on the generated image and the received feedback about the image via the user interface.

A further example embodiment provides a method that includes one or more of a generative artificial intelligence (GenAI) model to generate images based on user data using a dataset of images, executing the GenAI model based on input data from a user interface of a software application to generate an image corresponding to the input data, and displaying the image via a user interface of a software application, receiving feedback about the image via the user interface, and retraining the GenAI model based on the generated image and the received feedback about the image via the user interface.

A further example embodiment provides a computer-readable medium comprising instructions, that when read by a processor, cause the processor to perform one or more of a generative artificial intelligence (GenAI) model to generate images based on user data using a dataset of images, executing the GenAI model based on input data from a user interface of a software application to generate an image corresponding to the input data, and displaying the image via a user interface of a software application, receiving feedback about the image via the user interface, and retraining the GenAI model based on the generated image and the received feedback about the image via the user interface.

BRIEF DESCRIPTION OF THE DRAWINGS

FIGS. 1A-1B are diagrams illustrating a computing environment for generating goal-based imagery according to example embodiments.

FIG. 4 is a diagram illustrating a process of a generative artificial intelligence (GenAI) model generating a custom image based on prompts according to example embodiments.

FIG. 6B is a diagram illustrating a process of presenting identifiers of the predicted goals on a user interface according to example embodiments.

FIGS. 7A-7C are diagrams illustrating a process of generating a plurality of pseudo-accounts for a plurality of goals according to example embodiments.

FIG. 8 is a diagram illustrating a process of developing and implementing a generative artificial intelligence model according to example embodiments.

FIG. 9B is a diagram illustrating a method of predicting a goal of a user from user data according to example embodiments.

FIG. 9C is a diagram illustrating a method of gradually filling in a custom image based on progress toward a goal according to example embodiments.

FIG. 9D is a diagram illustrating a method of generating pseudo-data structures and images for a plurality of goals according to example embodiments.

DETAILED DESCRIPTION

Figure 1A:
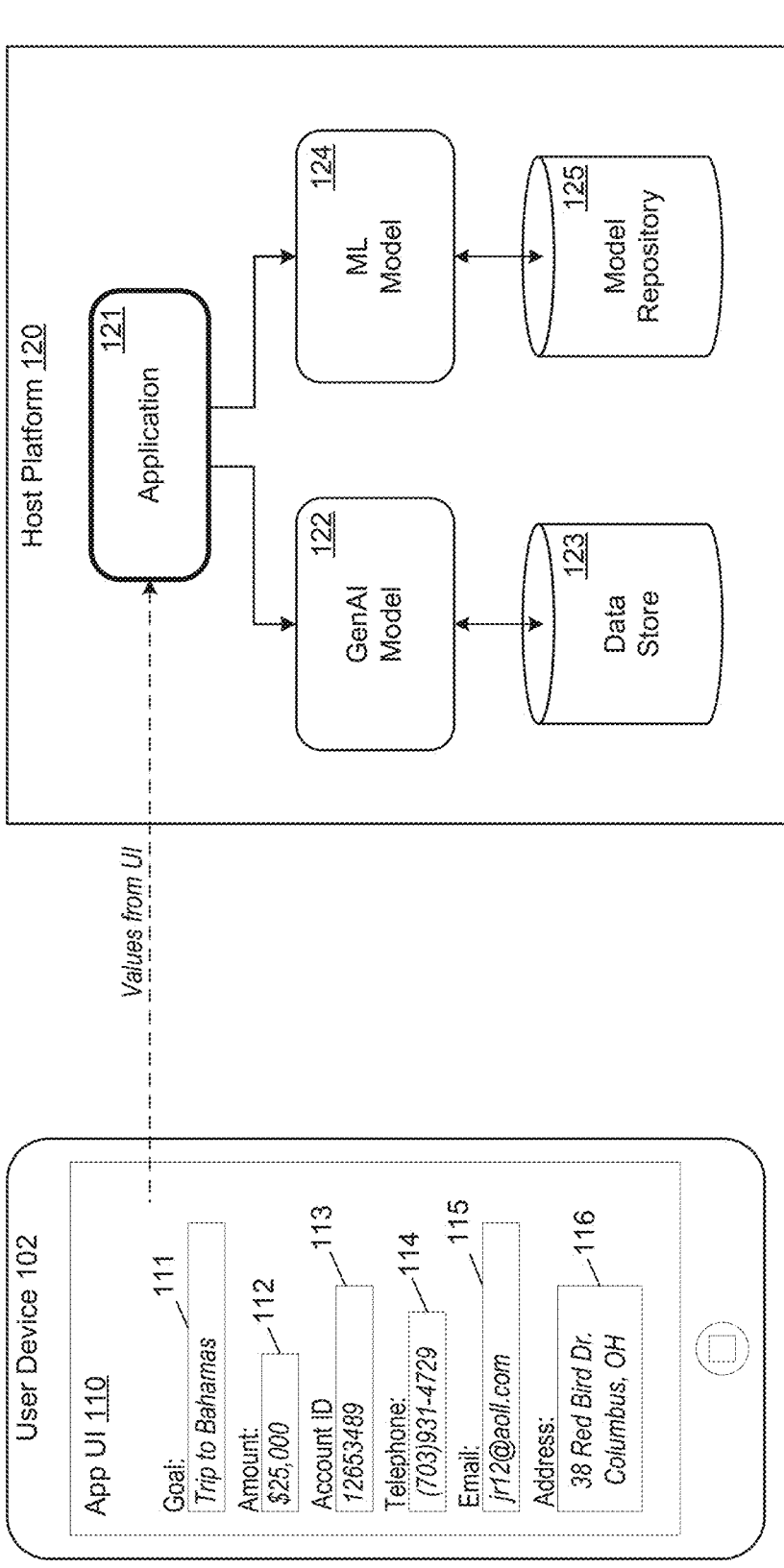

It is to be understood that although this disclosure includes a detailed description of cloud computing, implementation of the teachings recited herein is broader than a cloud computing environment. Rather, embodiments of the instant solution can be implemented in conjunction with any other type of computing environment now known or later developed.

The example embodiments are directed to a platform that generates custom imagery based on a future goal of a user. The custom imagery may be incorporated into a digital image, a hologram, a holograph, a cartoon, a video, a still image, or another artifact, which can be displayed on a user interface and delivered to a user device. The custom imagery may be generated by a generative artificial intelligence (GenAI) model trained based on a large corpus of images. In some embodiments, the GenAI model may be a large language model, such as a multimodal large language model. As another example, the GenAI model may be a transformer neural network ("transformer") or the like. The GenAI model is capable of understanding connections between text and images. For example, the GenAI model may include libraries and deep learning frameworks that enable the model to create realistic images from text inputs.

In some embodiments, the GenAI model may gradually fill in the content of the custom image over time. In this case, the image may be filled based upon a dynamic variable such as how much the user has saved towards the goal, how close the user is in time to the goal, etc.

In some cases, the rate at which the image is filled in may be dynamic because it depends on the rate at which the user saves toward the goal. For example, the model may receive an updated status of the user each day and fill in a ratio of pixels within the custom image based on a ratio of funds saved towards the goal that day. In some embodiments, the model can also remove segments of the image (i.e., previously rendered pixels) if the user gets farther away from the goal, such as spending money already dedicated to the goal or changing plans causing the goal to be later.

By creating goal-based imagery, the example embodiments enable the visual depiction of a user's goals. Research has proven that visualizing goals can enhance the chances of a user achieving those goals. The example embodiments are directed to a platform that generates a goal-based imager customized to a user, allowing the user to visualize and help obtain their goals. The custom image is an entirely new image that has never been generated before and is, therefore, unique. In some embodiments, the image may be a collage of integrated images.

For example, a user may be saving for a new automobile. The user may input data about the new automobile into the application as part of this process. In addition, other attributes of the user may also be available to the system, including family information, spending habits, browsing habits, etc. The user data may even include images of the user and the user's family. The model can generate a custom image of the family vacation (i.e., in the future).

The model may even include images of the family within the custom image. For example, the custom image may include an image of the family members on a beach at the upcoming family vacation location. In addition, attributes of the user, such as the user's browsing history and spending habits, can be input into the model and used by the model to add additional features to the custom images.

FIGS. 1A-1B illustrates examples of a computing environment for generating goal-based imagery according to example embodiments. For example, FIG. 1A illustrates a process 100A of a host platform 120, such as a cloud platform, web server, etc., interacting with a user device 102, such as a mobile device, a computer, a laptop, or the like. For example, the host platform 120 may host a software application 121 accessed by the user device 102 over a computer network such as the Internet. For example, the software application may be a mobile application with a front-end installed on the user device 102 and a back-end installed on the host platform 120. As another example, the software application 121 may be a progressive web application (PWA) hosted by the host platform 120 and made accessible to the user device 102 over the Internet.

In the example embodiments, the host platform 120 may include one or more generative artificial intelligence (GenAI) models, including GenAI model 122, which can prompt and generate custom imagery based on responses to the prompts. The host platform 120 may include one or more models, including a machine learning model 124. It should also be understood that the other models may also include artificial intelligence (AI) models, other GenAI models, and the like. The models, including the GenAI model 122 and the machine learning model 124, may be held by the host platform 120 within a model repository 125. In addition, the models, including the GenAI model 122 and the machine learning model 124, may have access to data stored in a data store 123 of the host platform 120.

The data store 123 may store user data, account data, transaction data, machine learning data, training data, retraining data, and the like. The data store 123 may be a cloud data store. The data store 123 may be accessed via an application programming interface (API). Although not shown, the host 10 at form 120 may also access one or more external systems (e.g., databases, websites, etc.) over a computer network and collect/retrieve data from the one or more external systems, including user data.

In this example, a user uses device 102 to request a new savings goal through an account shown on a user interface 110 of the software application 121 hosted by the host platform 120. Here, the user interface 110 may display a plurality of input fields, including a field 111, a field 112, a field 113, a field 114, a field 115, and a field 116, which request input from the user. The input fields may include input fields that request input data, such as the user's personal data. The input fields may also include "prompts." The input fields are designed to draw information from the user to generate custom imagery. In some embodiments, the imagery may be based on a goal of the user or a predicted goal of the user.

In FIG. 1A, the user has input a particular goal into the field 111 of the user interface 110 and a total amount needed to reach the total in the field 112. The user has also entered additional personal attributes of the user into the field 113, the field 114, the field 115, and the field 116. In this example, the data values within the fields on the user interface 110 are collected by the software application 121 on the host platform 120 and used to generate a custom image of the goal that the user has entered into the field 111 of the user interface 110. For example, the host platform 120 may execute one or more GenAI models on the input data to generate a custom image, as shown in FIG. 1B.

Although not shown in FIG. 1A, it should be appreciated that the input data used for generating the custom imagery may also be collected from a data source instead of a user interface. For example, the user data may be pulled from a database, a financial account, a transaction history, etc.

Referring now to FIG. 1B, a process 100B of generating a custom image 118 is shown according to various embodiments. In this example, the software application 121 calls a GenAI model 122 to generate a custom image based on the user's goal entered into the user interface 110 and the value needed to reach that goal. In this example, the goal relates to a family vacation the user is saving for this summer. The GenAI model 122 may receive the goal information in the form of text and convert the text into the custom image 118 of the goal in response. In the example of FIG. 1B, the custom image 118 is an image of the family's summer vacation. For example, the custom image 118 may include a picture of a beach at the location where the family wants to visit. The family could even be on the beach in the picture. The picture could be rendered as a video, a cartoon, a hologram, etc. The custom image 118 is unique in that no other image is like it. During the image generation process, user data from the data store 123 may be input to the GenAI model 122 along with the values from the user interface 110. The additional data from the data store 123 can further enhance the custom imagery.

The GenAI model 122 is trained to generate images from text. For example, the model may be embedded with mappings between texts and images. For example, the GenAI model 122 may be a large language model (LLM), such as a multimodal LLM. As another example, the GenAI model may be a transformative neural network (transformer) that uses deep learning methodologies to generate digital images from natural language descriptions referred to as prompts.

The GenAI model 122 is a text-to-image generation model that receives a description of an item and generates a custom image (unique image) that has never been generated before. The image may be generated based on the description and other information associated with the user, such as personal attributes/preferences of the user learned by the system over time, browsing habits of the user, etc.

In addition, the software application 121 may also use a machine learning model 124 to perform other predictive functionalities in combination with the image generation performed by the GenAI model 122. For example, the machine learning model 124 may identify user attributes from the browsing history. The attributes may include products, geographic locations, etc., of preference to the user that the GenAI model 122 can use to generate the custom images.

Figure 2:
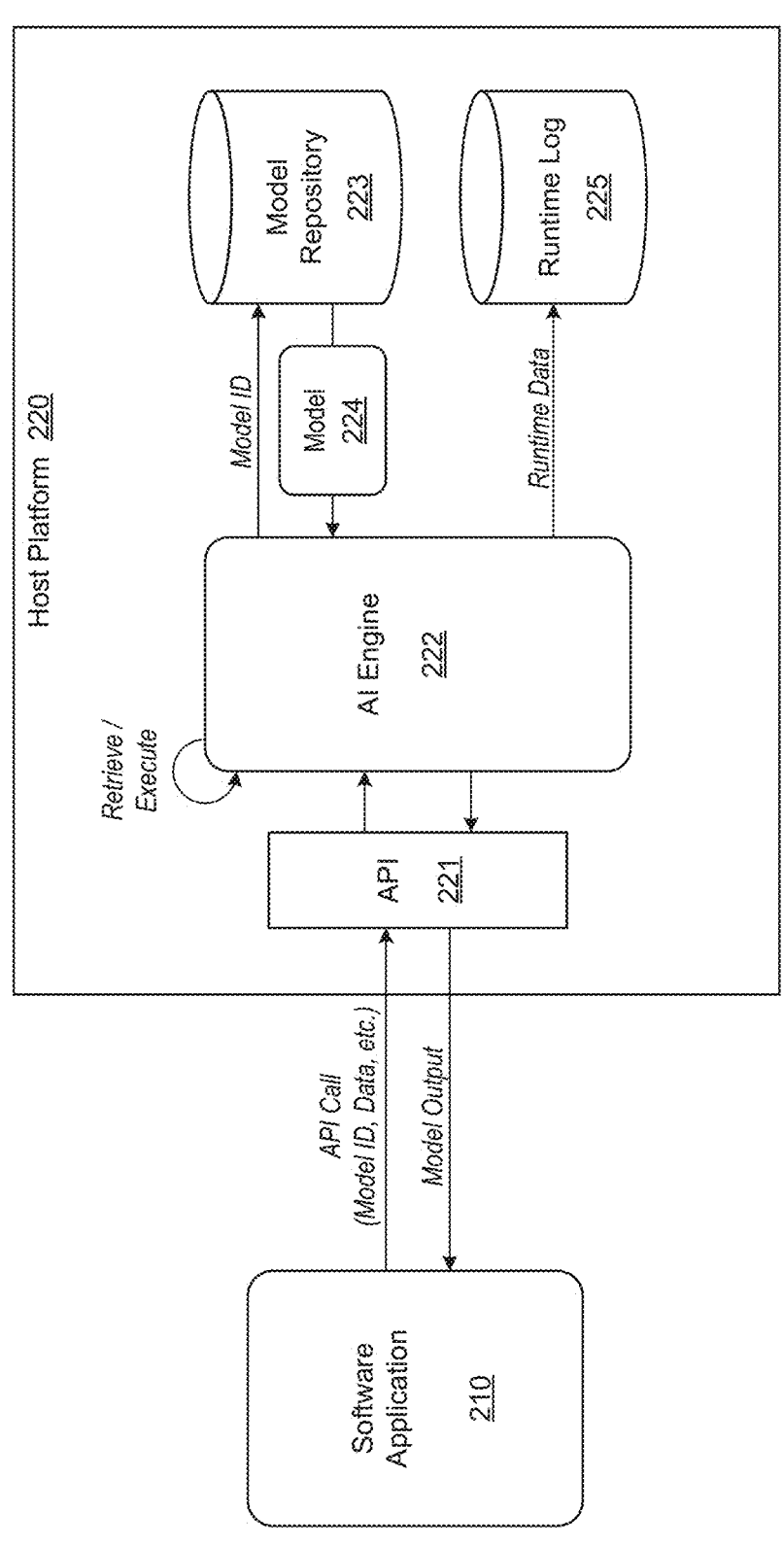
FIG. 2 is a diagram illustrating a process of executing a machine-learning model on input content according to example embodiments.

FIG. 2 illustrates a process 200 of executing a model 224 on input content according to example embodiments. Referring to FIG. 2, a software application 210 may request execution of the model 224 by submitting a request to the host platform 220.

In response, an AI engine 222 may receive the request and trigger the model 224 to execute within a runtime environment of the host platform 220. The process 200 may execute the GenAI model 122 and the machine learning model 124, as shown in FIGS. 1A and 1B. For example, each model may have a unique identifier that can be used to identify the model within a model repository 223.

In FIG. 2, the AI engine 222 may control access to and execution of models stored within the model repository 223. For example, the models may include GenAI models, AI models, machine learning models, neural networks, or the like. The software application 210 may trigger execution of the model 224 from the model repository 223 via submission of a call to an API 221 (application programming interface) of the AI engine 222. The request may include an identifier of a model or models to be executed, a payload of data (e.g., to be input to the model during execution), and the like. The AI engine 222 may retrieve the model 224 from the model repository 223 in response, deploy the model 224 within a live runtime environment, execute the model 224 on the payload of data, and return a result of the execution to the software application 210.

In some embodiments, the payload of data may be in a format that cannot be input to the model 224 nor read by a computer processor. For example, the payload of data may be in text format. In response, the AI engine 222 may convert the data payload into a format readable by the model 224, such as a vector or other encoding. The vector may then be input to the model 224.

In some embodiments, the software application 210 may display a user interface that enables a user to provide feedback from the output provided by the model 224. For example, a user may input a confirmation that the predicted image of a goal generated by a GenAI model is correct or is liked. This information may be added to the results of execution and stored within a log 225. The log 225 may include an identifier of the input, an identifier of the output, an identifier of the model used, and feedback from the recipient. This information may be used to retrain the model subsequently.

Figure 3A:
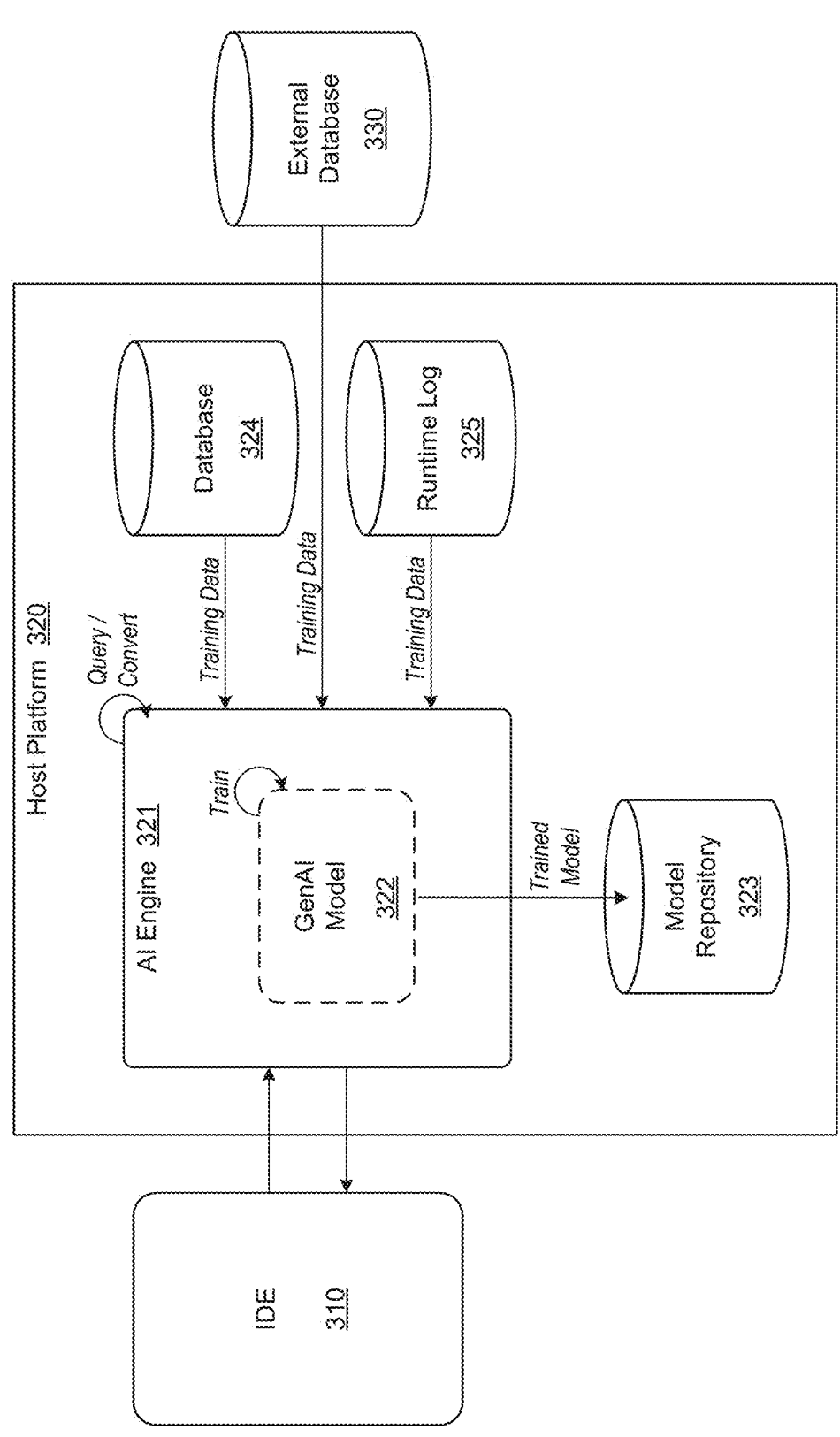
FIGS. 3A-3C are diagrams illustrating processes for training a machine learning model according to example embodiments.

FIG. 3A illustrates a process 300A of training a GenAI model 322 according to example embodiments. However, the process 300A, shown in FIG., should be appreciated. 3A also applies to other models, such as machine learning models, AI models, and the like. Referring to FIG. 3A, a host platform 320, may host an IDE 310 (integrated development environment) where GenAI models, machine learning models, AI models, and the like may be developed, trained, retrained, and the like. In this example, the IDE 310 may include a software application with a user interface accessible by a user device over a network or through a local connection.

For example, the IDE 310 may be embodied as a web application that can be accessed at a network address, URL, etc., by a device. As another example, the IDE 310 may be locally or remotely installed on a computing device used by a user.

The IDE 310 may be used to design a model (via a user interface of the IDE), such as a generative artificial intelligence model that can receive text as input and generate custom imagery, etc. The model can then be executed/trained based on the training data established via the user interface. For example, the user interface may be used to build a new model. The training data for training such a new model may be provided from a training data store such as a database 324, which includes training samples from the web, customers, and the like. As another example, the training data may be pulled from one or more external data stores 330, such as publicly available sites.

The GenAI model 322 may be executed on training data via an AI engine 321 of the host platform 320 during training. The training data may include a large corpus of generic images and text that is related to those images. The GenAI model 322 may learn mappings/connections between text and imagery during the execution. When fully trained, the model may be stored within the model repository 323 via the IDE 310 or the like.

As another example, the IDE 310 may be used to retrain the GenAI model 322 after the model has already been deployed. Here, the training process may use executional results that have already been generated/output by the GenAI model 322 in a live environment (including any customer feedback, etc.) to retrain the GenAI model 322. For example, predicted outputs/images custom generated by the GenAI model 322 and the user feedback of the images may be used to retrain the model to enhance the images generated for all users. The responses may include requests for more color, different colors, different items, etc. This data may be captured and stored within a runtime log 325 within the live environment. The runtime log 325 can subsequently be used to retrain the GenAI model 322.

Figure 3B:
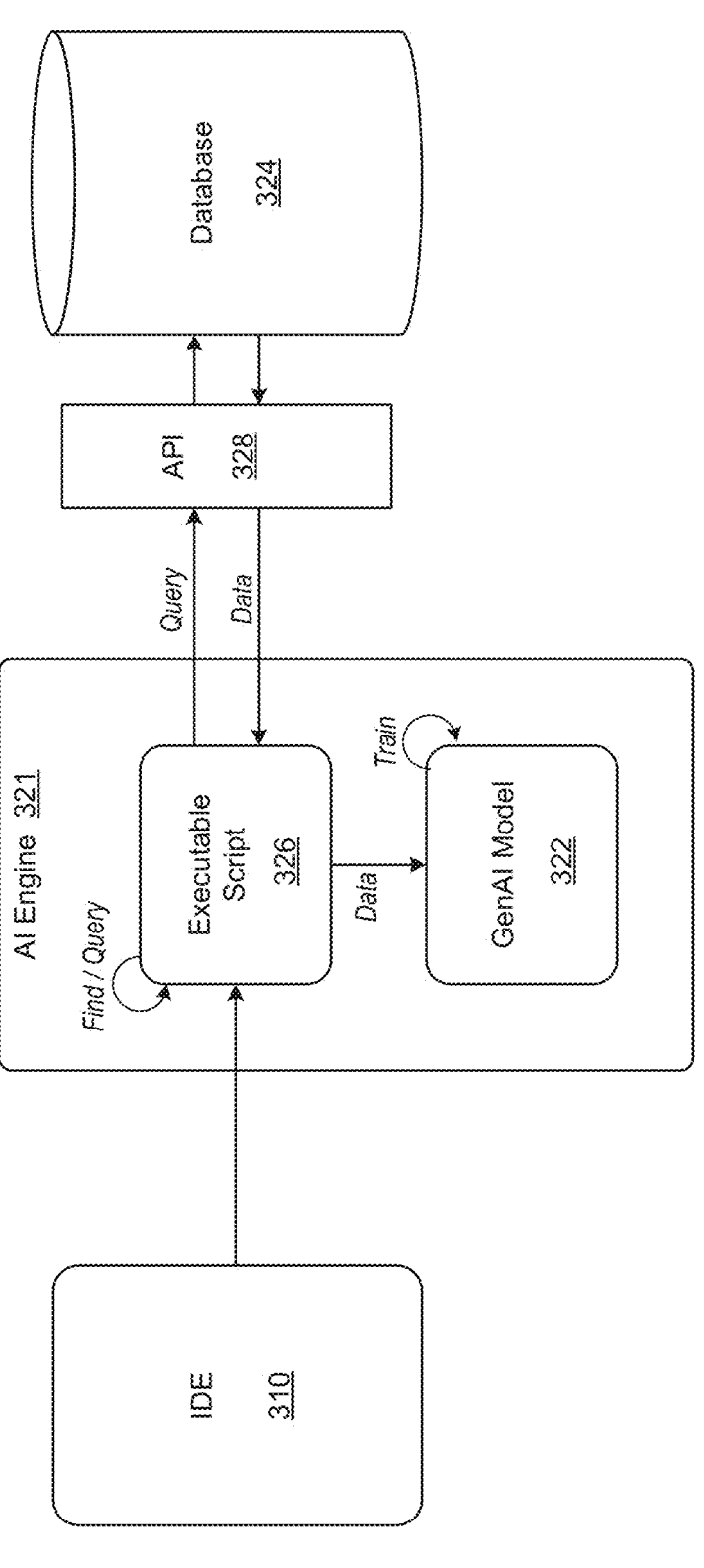

FIG. 3B illustrates a process 300B of executing a training process for training/retraining the GenAI model 322 via an AI engine 321. In this example, a script 326 (executable) is developed and configured to read data from a database 324 and input the data to the GenAI model 322 while the GenAI model is running/executing via the AI engine 321.

For example, the script 326 may use identifiers of data locations (e.g., table IDs, row IDs, column IDs, topic IDs, object IDs, etc.) to identify locations of the training data within the database 324 and query an API 328 of the database 324. In response, the database 324 may receive the query, load the requested data, and return it to the AI engine 321, which is input to the GenAI model 322. The process may be managed via a user interface of the IDE 310, which enables a human-in-the-loop during the training process (supervised learning). However, it should also be appreciated that the system is capable of unsupervised learning.

The script 326 may iteratively retrieve additional training data sets from the database 324 and iteratively input the additional training data sets into the GenAI model 322 during the execution of the model to continue to train the model. The script may continue until instructions within the script tell the script to terminate, which may be based on a number of iterations (training loops), total time elapsed during the training process, etc.

Figure 3C:
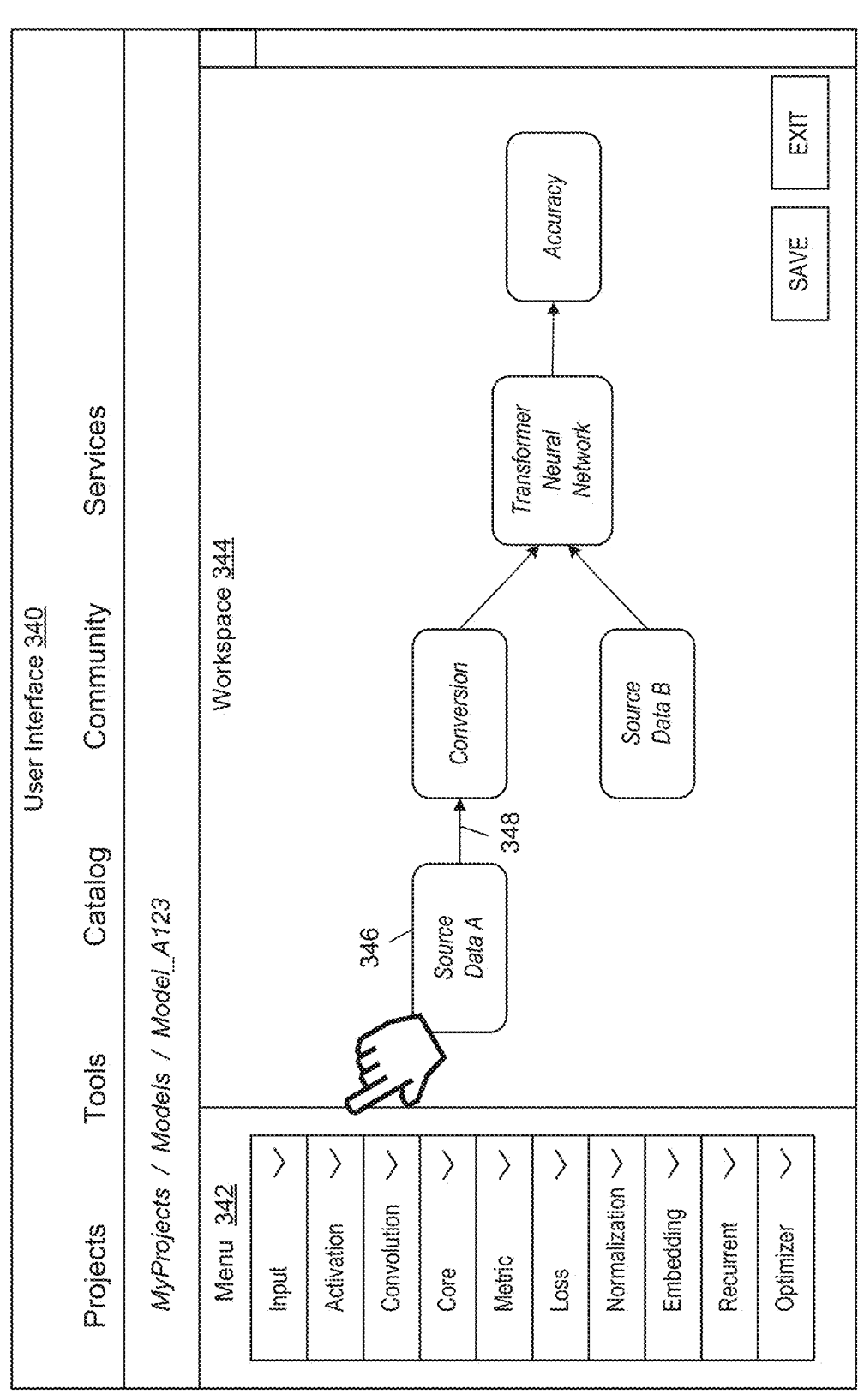

FIG. 3C illustrates a process 300C of designing a new AI model via a user interface 340 according to example embodiments. For example, the user interface 340 may be output as part of the software application that interacts with the IDE 310 shown in FIG. 3A, however, embodiments are not limited thereto. Referring to FIG. 3C, a user can use an input mechanism to make selections from a menu 342 shown on the left-hand side of the user interface 340 to add pieces to the model such as data components, model components, analysis components, etc., within a workspace 344 of the user interface 340.

In the example of FIG. 3C, the menu 342 includes a plurality of graphical user interface (GUI) menu options which can be selected to drill down into additional components that can be added to the model design shown in the workspace 344. Here, the GUI menu options include options for adding features such as neural networks, machine learning models, AI models, data sources, conversion processes (e.g., vectorization, encoding, etc.), analytics, etc. The user can continue to add features to the model and connect them using edges or other means to create a flow within the workspace 344. For example, the user may add a node 346 to a new model diagram within the workspace 344. For example, the user may connect the node 346 to another node in the diagram via an edge 348, creating a dependency within the diagram. When the user is done, the user can save the model for subsequent training/testing.

According to various embodiments, the GenAI model described herein may be trained based on custom-defined prompts designed to draw out specific attributes associated with a user's goal. These same prompts may be output during the live execution of the GenAI model. For example, a user may input a goal description and other attributes.

The GenAI model can then use the description/attributes to generate a custom image that enables the user to visualize the goal. The prompts may be generated via prompt engineering that can be performed through the model training process, such as the model training process described above in the examples of FIGS. 3A-3C.

Prompt engineering is structuring sentences (prompts) so the GenAI model understands them. A prompt may include a description of a goal, such as a goal of purchasing a particular type of car. The prompt may also provide the car's color, year, make, and model.

All of this information may be input into the GenAI model and used to create a custom image of the goal to enable the user to visualize the goal. Part of the prompting process may include delays/waiting times intentionally included within the script so the model has time to think/understand the input data.

FIG. 4 illustrates a process 400 of a GenAI model 422 generating a custom image 424 based on prompts according to example embodiments.

Referring to FIG. 4, the GenAI model 422 may be hosted by a host platform and may be part of a software application 420 that is also hosted on the host platform. Here, the software application 420 may establish a connection with a user device 410, such as a secure network connection. The secure connection may include a PIN, biometric scan, password, username, TTL handshake, etc.

In the example of FIG. 4, the software application 420 may control the interaction of the GenAI model 422 on the host platform and the user device 410. In this example, the software application 420 may output queries on a user interface 412 of the user device 410 with user information requests. The user may enter values into the fields on the user interface corresponding to the queries, and submit/transfer the data to the software application 420, for example, by pressing a submit button, etc.

In this example, the application may combine the query with the response from the user interface and generate a prompt submitted to the GenAI model 422. For example, each prompt may include a combination of a query on the UI plus the response from the user. For example, if the query is "Describe a Goal to Save For" and the response is "A Cruise to Alaska," then the text from both the query and the response to the query may be added to the prompt and submitted to the GenAI model 422.

In some embodiments, the software application 420 may deliberately add waiting times between submitting prompts to the GenAI model 422 to ensure the model has enough time to "think" about the answer. The waiting times may be integrated into the code of the software application 420, or they may be modified/configured via a user interface. Furthermore, the ordering of the prompts and the follow-up questions may differ depending on the answers given during the previous prompt or prompts. The content within the prompts and the ordering of the prompts can cause the GenAI model 422 can create custom images. Each prompt may include multiple components, including one or more of context, an instruction, input data, and an expected response/output.

In some embodiments, the custom image generated herein may gradually fill in over time. For example, pixels within the custom imagery may be filled in based on how close the user is to obtaining a particular goal. Here, the number of pixels that are filled in may depend on how much a user has saved towards the goal, how much time still needs to go by before the goal arrives, etc. Thus, the image can be filled dynamically based on another dynamic condition. Examples of filling in a custom image based on conditions are further described in the examples of FIGS. 5A-5F.

Figure 5A:
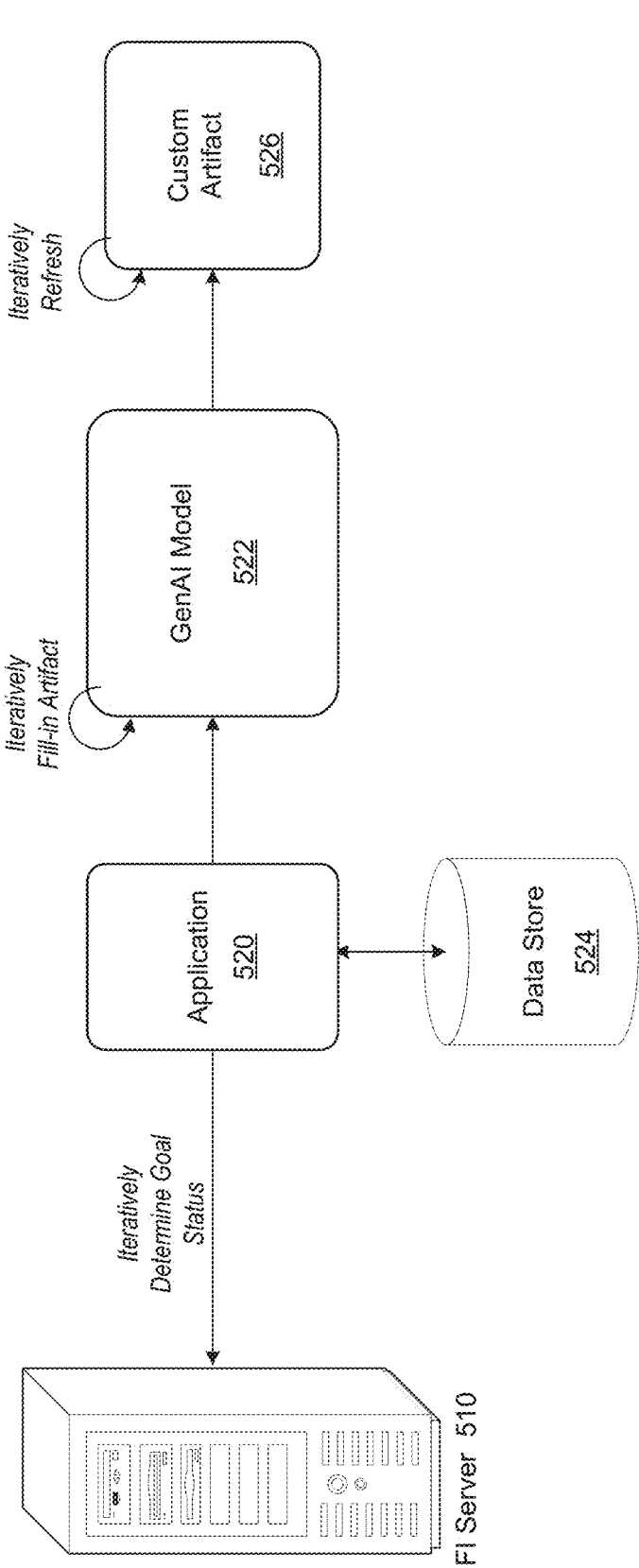
FIGS. 5A-5F are diagrams illustrating a process of filling in a custom-image over time based on dynamic data according to example embodiments.

FIG. 5A illustrates a process 500 of incrementally filling in a custom artifact, such as a custom image of a goal. Referring to FIG. 5A, a software application 520, may generate goal-based artifacts based on goals generated by a user. In this example, the software application 520 collects data about a user, such as from a UI, a user device, a transaction history, a browsing history, etc. It builds a custom artifact 526 based thereon via execution of a GenAI model 522 on the collected data. The custom artifact 526 may include a digital image, a video, a cartoon, a hologram, or the like.

According to various embodiments, rather than display the custom artifact 526 all at once. The example embodiments can gradually fill in the custom artifact (e.g., pixels of the artifact) as the user gets closer to reaching their goal.

That is, the user's pursuit of a goal that the custom image is generated based upon may be monitored by the software application 520 and may trigger the rate at which the software application 520 fills in the custom artifact 526. For example, the software application 520 may monitor a user's financial account, such as a savings account, to see how close the user is to an amount of funds needed for the goal. The financial progress of the user towards accomplishing the goal may be analyzed and used to fill in the custom artifact 526 at the same rate of progress.

For example, if the user has saved 75% of the funds needed for a new home, an artifact depicting the goal of buying the new home may have 75% of its pixels filled in, leaving the remaining 25% blank or empty data.

The application 520 may store account information and login credentials for accessing the user's bank account within a data store 524. The software application 520 may use this information to query a server 510 of a financial institution (FI) that hosts the user's bank account. The software application 520 may also register to receive notifications from the server 510 each time the user's bank account is updated. The software application 520 may reveal an additional image segment (a subset of pixels) each time the user adds money saved towards the goal into the user's bank account.

In this way, the custom artifact 526 can be filled in/updated in real-time to represent a current status of the user's progress towards saving the needed funds for the goal, which can include removing pixels from the image when the user spends money that was previously set aside for the goal. The custom artifact 526 may be stored at the host platform and downloaded/delivered to the user device via email, SMS, etc.

Each time the custom artifact 526 is modified (e.g., filled in more) by the software application 520, the custom artifact 526 may be refreshed at the host platform, causing the updates to be integrated into the custom artifact 526. Furthermore, the updated image may be sent to the user device.

Figure 5C:
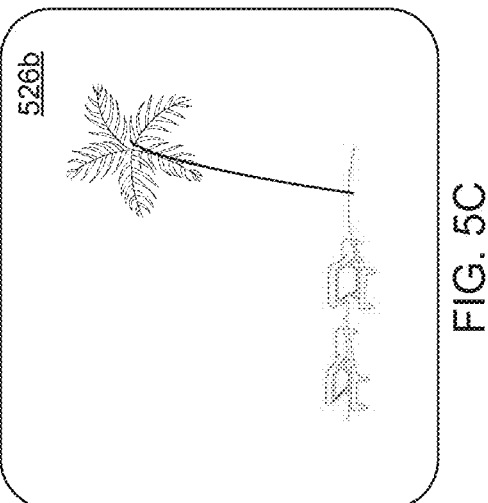
Figure 5E:
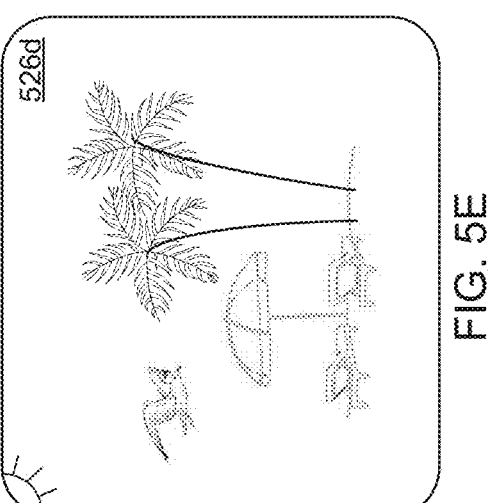
Figure 5B:
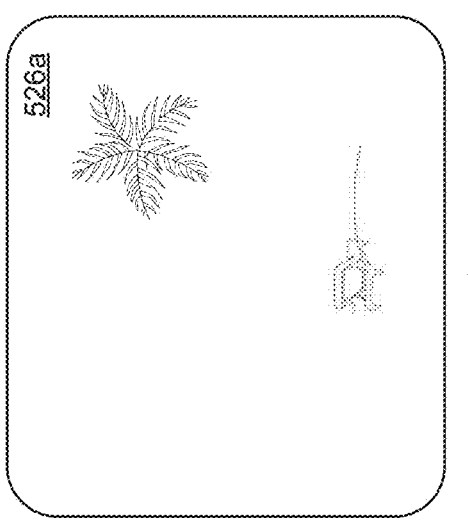

FIGS. 5B, 5C, 5D, and 5E illustrate different fill levels for the custom artifact 526 shown in FIG. 5A. For example, FIG. 5B illustrates a partially filled-in custom artifact 526a after the user has saved 20% toward their desired goal of $25,000. In this example, the GenAI model 522 has generated a custom image of a family vacation on the beach. Still, the software application 520 has only filled in a few components of the custom image, including a beach chair and part of a palm tree.

Meanwhile, FIG. 5C illustrates another partially filled-in custom artifact, 526b, after the user has saved 50% toward their desired goal of $25,000. The software application 520 has further filled in the custom image to include the rest of the palm tree, another beach chair, and sand.

Figure 5D:
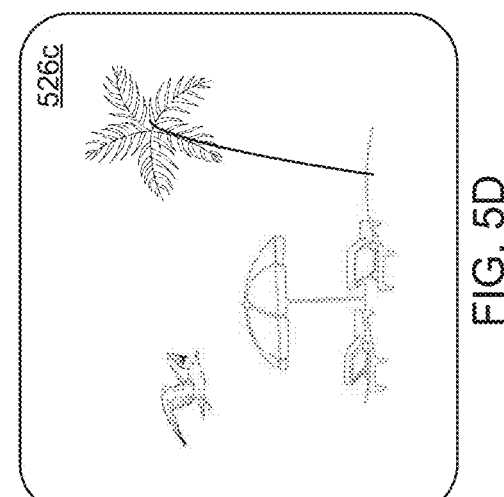

FIG. 5D illustrates another partially filled-in custom artifact, 526c, after the user has saved 70% of their desired goal. The software application 520 has filled an umbrella between the beach chairs and a seagull in the sky. Furthermore, FIG. 5E illustrates a completely filled-in custom artifact 526d in response to the user completing their savings goal (100%).

Figure 5F:
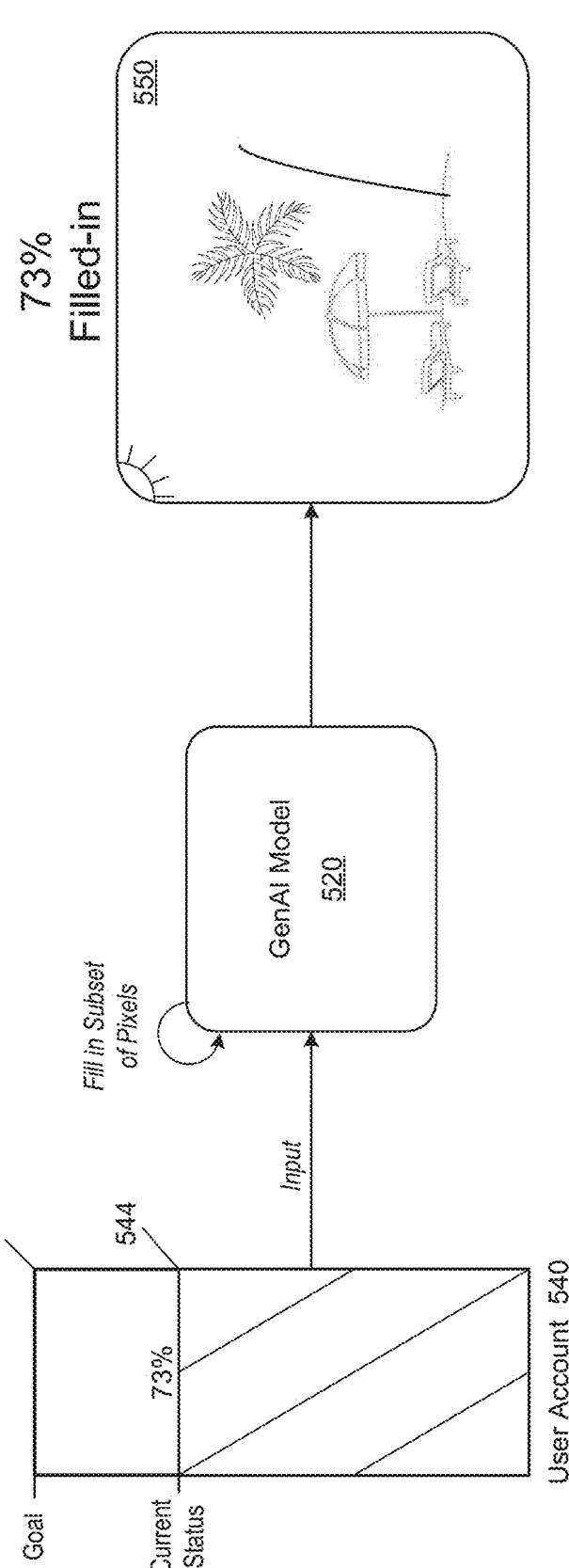

FIG. 5F illustrates a process 530 of filling in a custom image 550 based on a user's current status toward their goal 542. The current status may be measured by a current amount 544 in the user's bank account. In this case, the current status is that the user has saved 73% of the necessary funds for the goal. This information may be obtained from a user account page 540 of a software application or other software program. In response, the software application 520 can control the GenAI model 522 to reveal only 73% of the custom image 550, thus enticing the user to complete the rest of the goal and see the rest of the custom image 550.

Figure 6A:
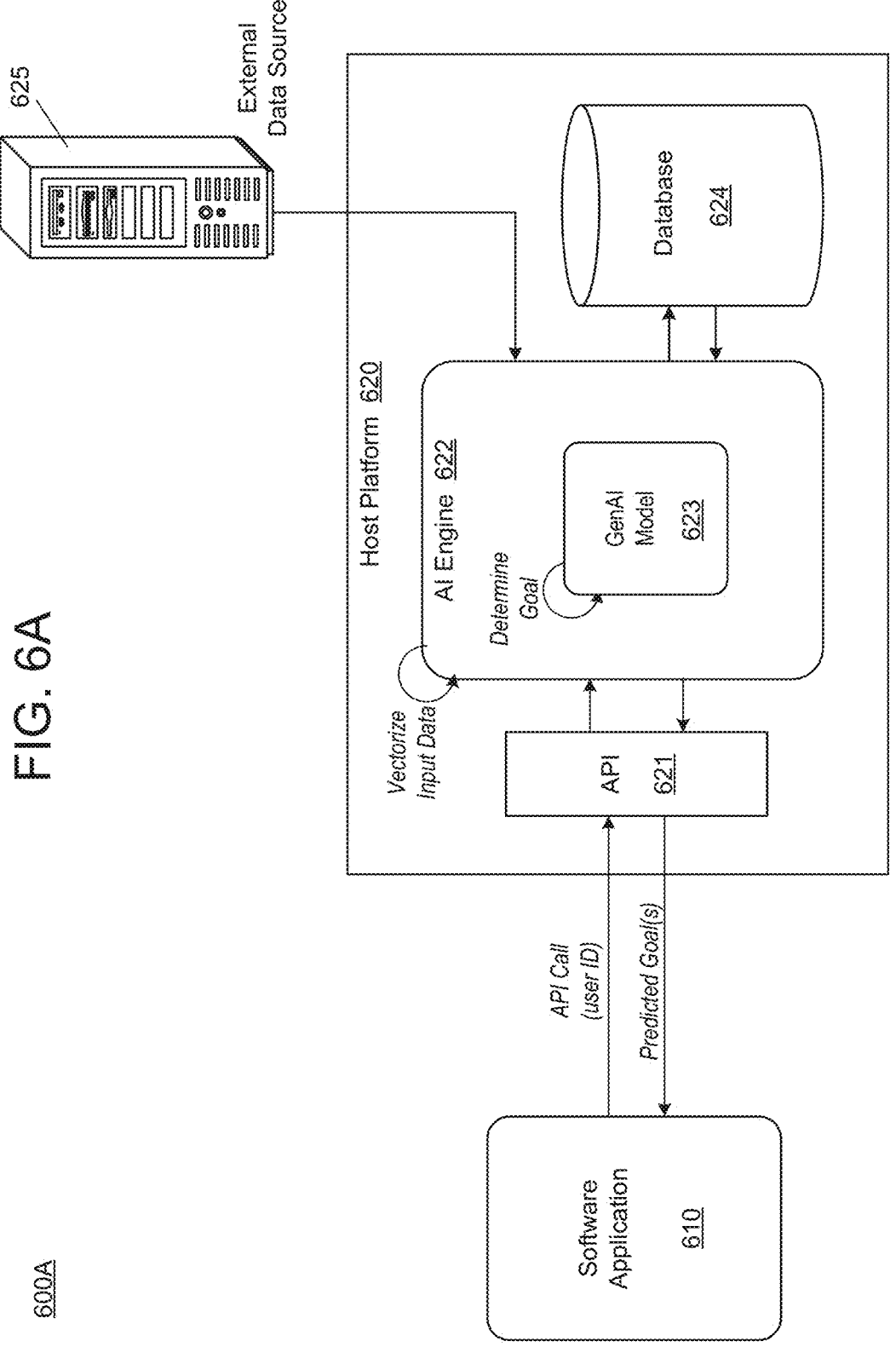
FIG. 6A is a diagram illustrating a process of predicting goals for a user according to example embodiments.
Figure 6B:
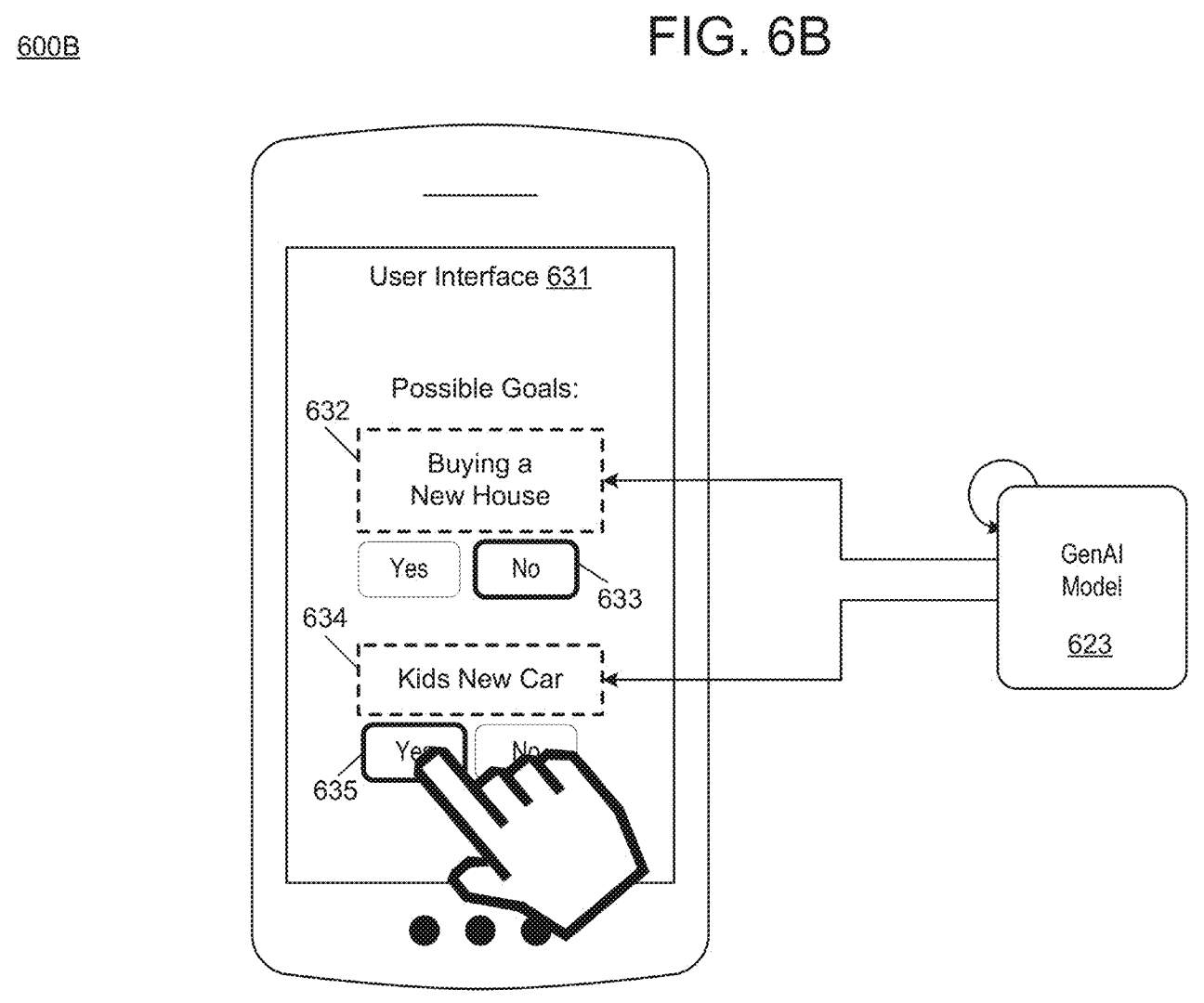

FIG. 6A illustrates a process 600A of predicting goals for a user according to example embodiments and FIG. 6B illustrates a process 600B of presenting/rendering identifiers of the predicted goals on a user interface 631 according to example embodiments.

Referring to FIG. 6A, a host platform 620 may host a GenAI model 623 that can ingest user data such as transaction history data from a user's bank account and predict goals of the user (e.g., predict the user wants to save for a vacation based on travel tickets purchased, etc.).

As another example, the user data may include personal information about the user, the user's family, employment, etc., and the GenAI model can predict life-related goals associated with such personal information (e.g., saving for college, etc.).

For example, a software application 610 may query an AI engine 622 of the host platform 620 with an identifier of the user and/or the user's bank account. The query may be received via an API 621 of the AI engine 622. In this example, the AI engine 622 can retrieve user data from an external data source 625 and input the user data into the GenAI model 623, which can predict a future goal of the user based on this data. As another example, the AI engine 622 can retrieve user data from a database 624 of the host platform 620 and use this user data to predict the goal(s) of the user.

For example, the GenAI model 623 may detect that the user has a goal, such as saving for a family vacation and a point in time when the goal needs to be achieved (e.g., July 1st, etc.) based on the previous transaction history of the user showing the family usually goes on vacation in July every year. The GenAI model 623 may consume the text from the transaction history and output a suggested goal and suggested points when the user should reach the goal.

The system described herein may further learn from the predicted goals in some embodiments. For example, as shown in FIG. 6B, an identifier 632 of a first predicted goal, and an identifier 634 of a second predicted goal are displayed on a user interface 631 of a user device corresponding to the user for whom the goal is predicted. In this example, the user interface 631 also includes buttons 633 and 635 that enable feedback about the predicted goals. The feedback and the predicted goals can be used to retrain the model to refine the model further.

Figure 7A:
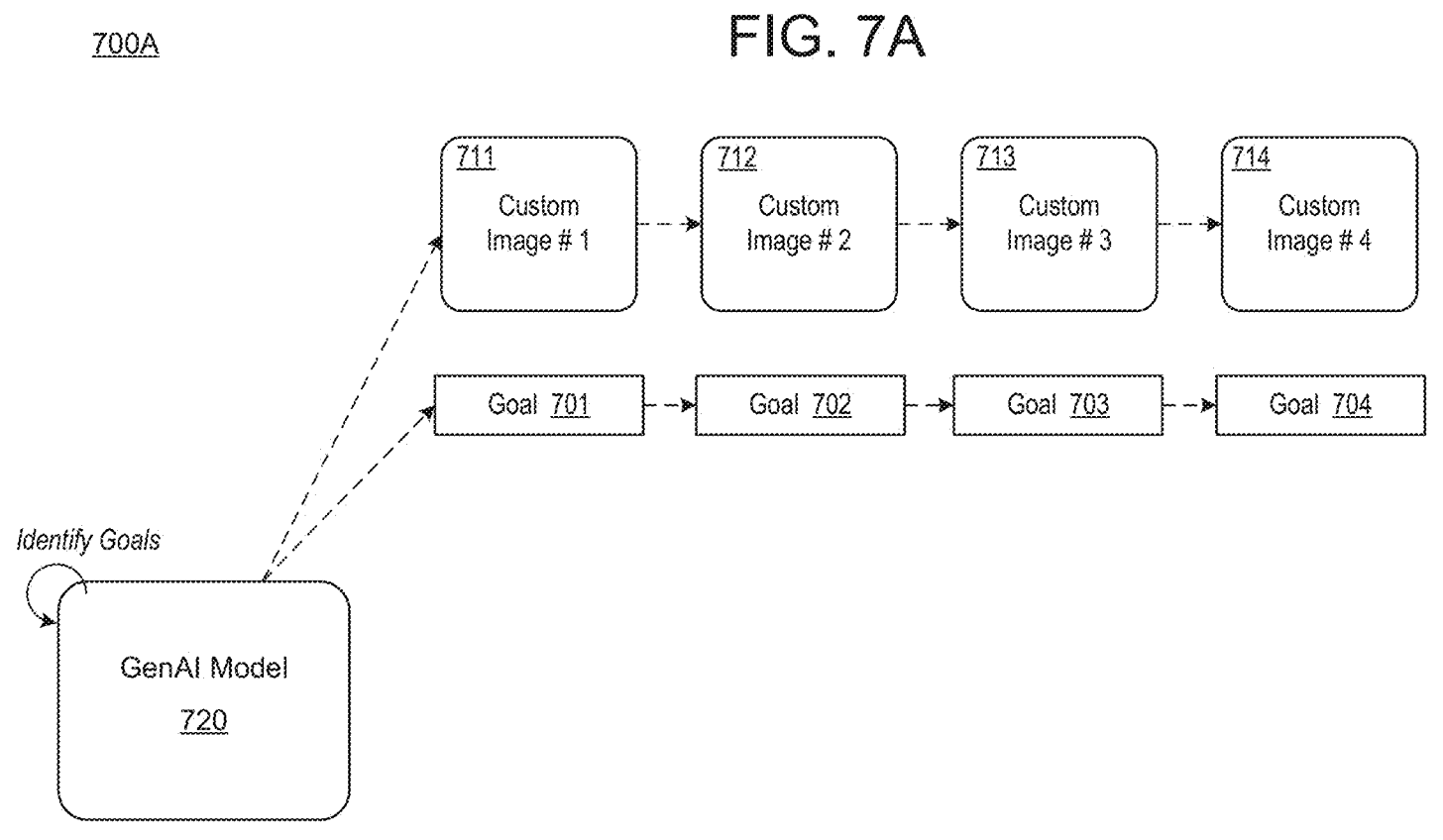
Figure 7B:
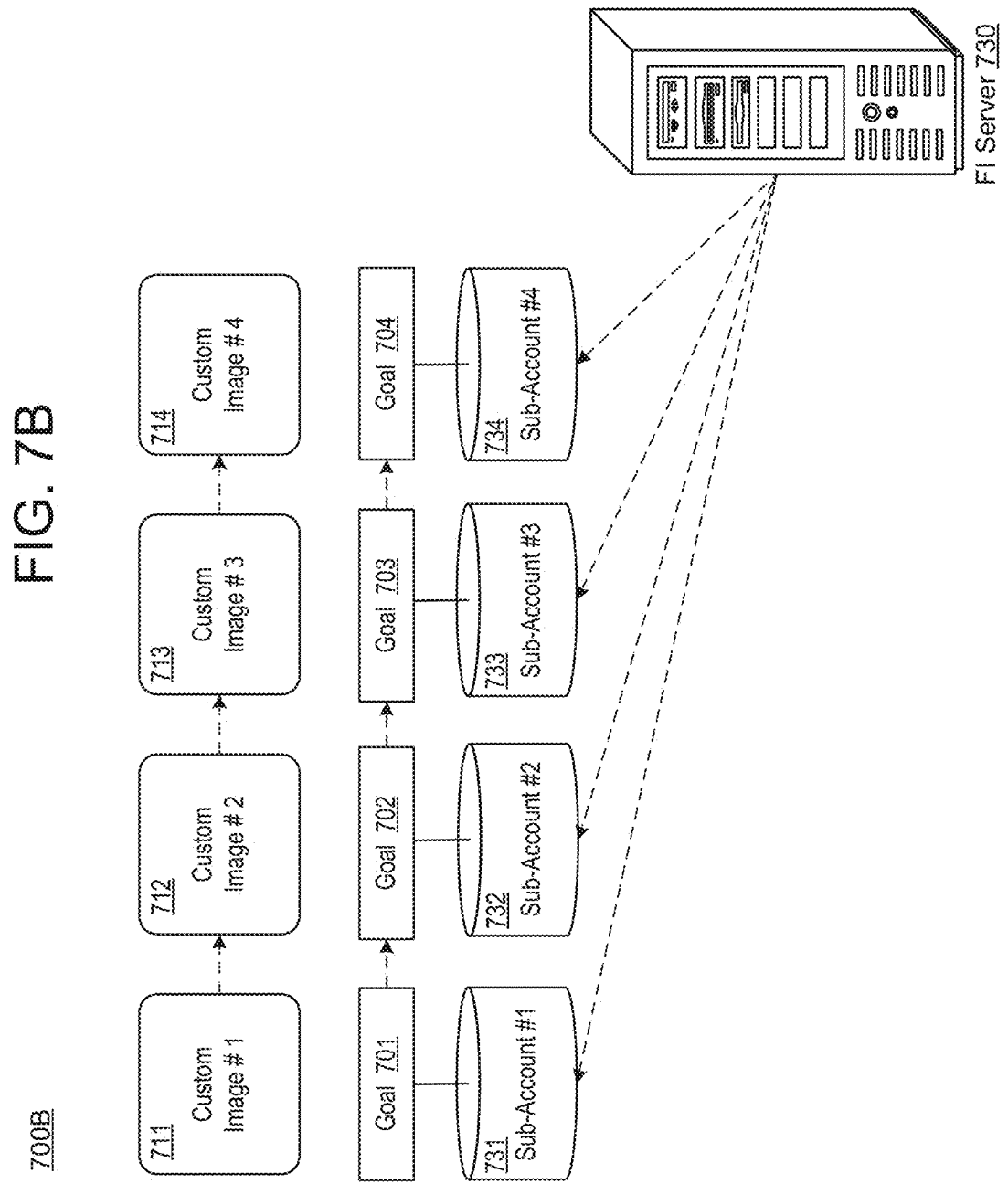
Figure 7C:
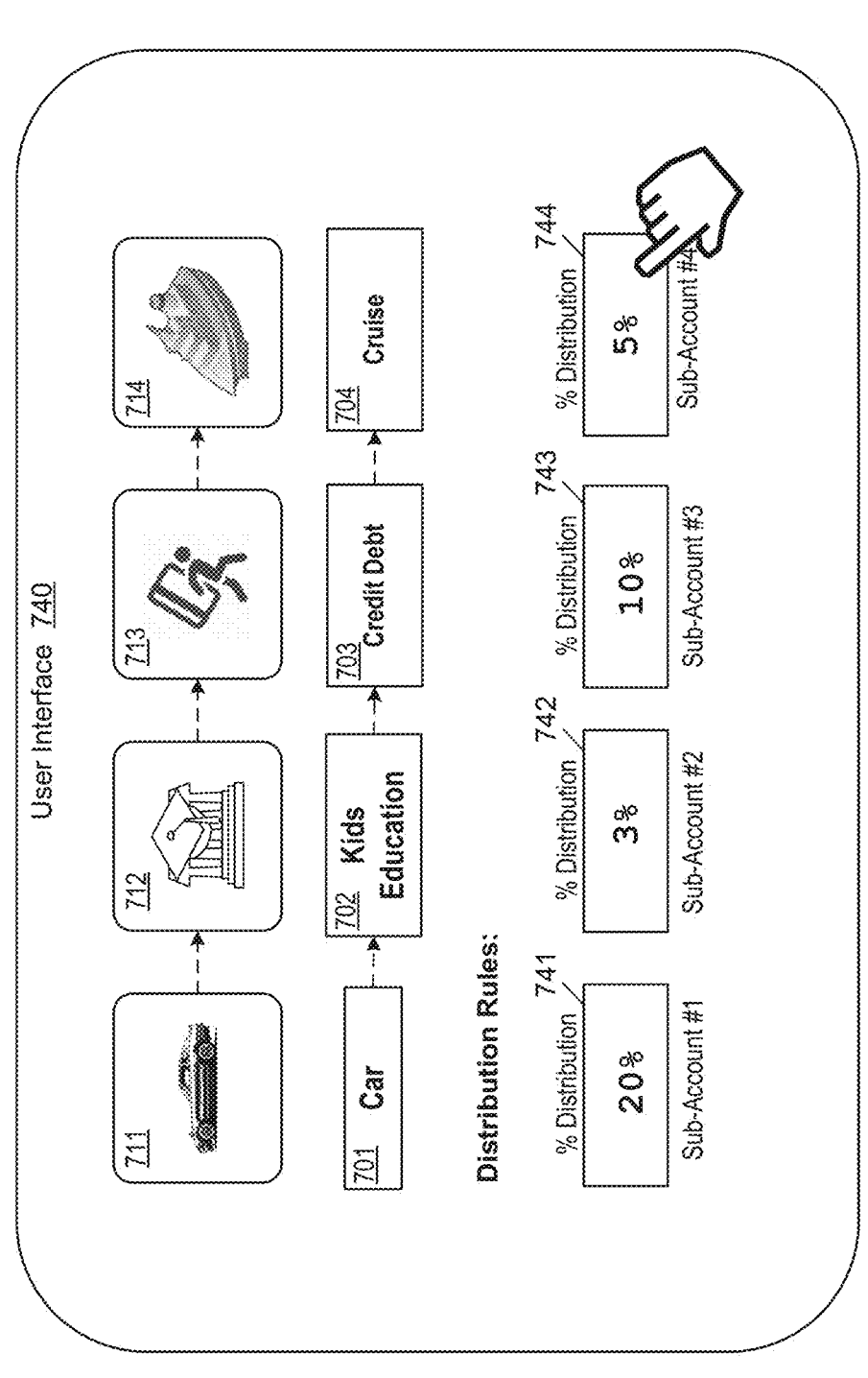

FIGS. 7A-7C illustrates a process of managing a plurality of goals for a user with a plurality of custom imagery according to example embodiments. For example, the process in FIG. 6A may be used to identify multiple goals of the user, which can be visualized simultaneously on a user interface. For example, FIG. 7A illustrates a process 700A of generating a plurality of custom images 711, 712, 713, and 714 for a plurality of goals 701, 702, 703, and 704, respectively. Each custom image may be generated by executing a GenAI model 720 on a description of a corresponding goal. The GenAI model 720 may generate the plurality of custom images 711, 712, 713, and 714 based on the respective descriptions of the plurality of goals 701, 702, 703, and 704 and other data such as user data collected from the user or external data sources.

FIG. 7B illustrates a process 700B of a financial server 730 working with the GenAI model 720 shown in FIG. 7A to generate a plurality of pseudo-accounts 731, 732, 733, and 734, corresponding to the plurality of goals 701, 702, 703, and 704, respectively, and corresponding to the plurality of custom images 711, 712, 713, and 714, respectively. Each pseudo-account may be a dummy account for financial management purposes and linked to the user's bank account. In other words, the pseudo-accounts may be used within the software for managing money and may only be used for account management purposes. As such, the pseudo-accounts may not be assigned account numbers but pseudo-identifiers that are random or arbitrary values that can be used to identify the pseudo-accounts in a data store.

FIG. 7C illustrates a process 700C of rendering a user interface 740 with the plurality of custom images 711, 712, 713, and 714, filled in with content, and the plurality of goals 701, 702, 703, and 704 filled in with text content.

Thus, the user can visualize what each goal corresponds to. While each of the images is filled in in this example, it should also be appreciated that the custom images may be filled in dynamically based on progress towards a goal. The progress can be measured from account history data, etc.

The user interface 740 also includes a plurality of fields 741, 742, 743, and 744 for defining distribution rules for the plurality of pseudo-accounts 731, 732, 733, and 734, respectively. The user can use an input mechanism such as a mouse, keyboard, pointer, etc., to enter the distribution ratio into the plurality of fields 741, 742, 743, and 744. Not all of the funds need to be distributed. Thus, the user can manage the disbursement of funds towards various goals on a dynamic and ever-evolving basis via the user interface 740.

FIG. 8 illustrates a process 800 of developing and implementing a generative artificial intelligence model according to example embodiments. Referring to FIG. 8, in 801, a new generative AI model (GenAI) may be developed via an IDE of a system, etc. For example, the GenAI model may be a large language model, a transformer neural network, etc. In 802, the GenAI model may be trained using a large corpus of images associated with the text.

Through this process, the GenAI model learns to connect text pieces to imagery types. In 803, the system may receive user data, for example, in a request from a software application or other process. In 804, the system may execute the trained GenAI model on the data to generate a custom image from the user data. The custom image may include imagery based on the user's goal obtained from prompts provided by a user interface of a software application on a device of the user.

In 805, the system may display the custom image on the software application's user interface on the user's device. In 806, the system may receive feedback from the user interface on the user's device. The feedback may indicate whether the user likes the custom image. The feedback may also include additional suggestions, such as data features to include, data features to remove, colors to use, colors to remove, etc. This data can be converted into prompts and retrain the GenAI model in 807. The software may repeat steps 803 to 807. Here, the user may have the option to continue to generate more feedback.

Thus, the GenAI model can be retrained based on its output and the feedback from a user concerning that output. In 808, the system may receive additional user data that may be collected from the user interface or a data store and execute the GenAI model again in 809 to generate another custom image.

Figure 9A:
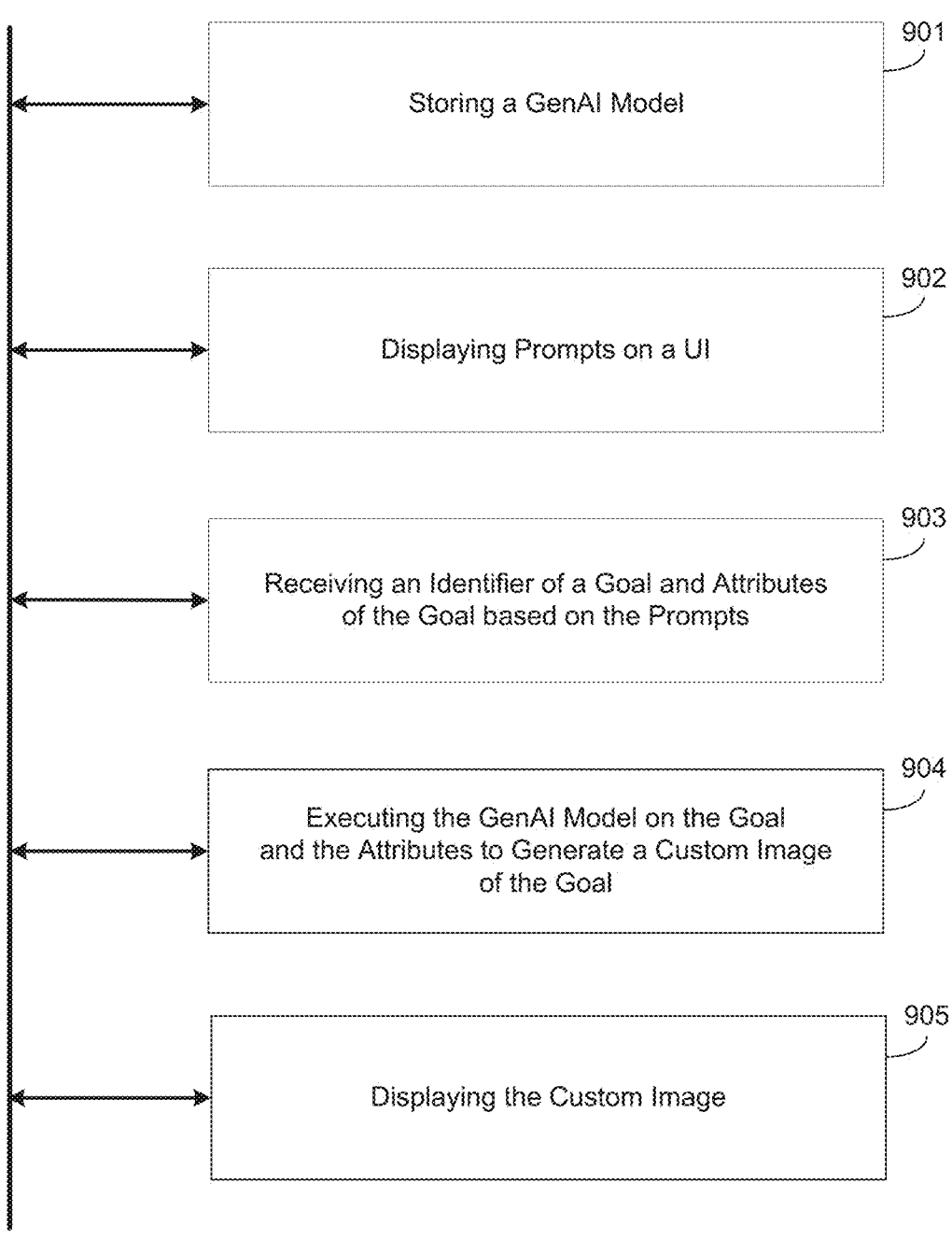
FIG. 9A is a diagram illustrating a method of generating a customized image according to example embodiments.

FIG. 9A illustrates a method 900 of generating a customized image according to example embodiments. For example, the method 900 may be performed by a computing system, a software application, a server, a cloud platform, a combination of systems, and the like.

Referring to FIG. 9A, in 901, the method may include storing a generative artificial intelligence (GenAI) model configured to create images. In 902, the method may include displaying a plurality of prompts on a software application's user interface. In 903, the method may include receiving an identifier of a goal of the user and attributes of the goal via the plurality of prompts on the user interface. In 904, the method may include executing the GenAI model on the user's identifier and the goal's attributes to generate a custom image of the goal for the user. In 905, the method may include displaying the custom image of the goal via the software application's user interface.

In some embodiments, the executing may include generating a first partial image of the custom image via the execution of the GenAI model and displaying the first partial image of the goal via the software application's user interface.

In some embodiments, the method may further include detecting subsequent account activity of the user after displaying the first partial image and, in response, executing the GenAI model on the subsequent account activity of the user to generate a second partial image of the goal with additional data points filled-in in comparison to the first partial image of the goal.

In some embodiments, the identifier of the goal may include an identifier of a purchased item, and the executing comprises executing the GenAI model on the identifier of the purchased item and based on attributes of the purchased item.

In some embodiments, the attributes of the goal may include a current amount of savings in an account for the purchased item, and the processor is configured to execute the GenAI model to fill in a percentage of the custom image based on the current amount of savings in the account for the purchased item to generate the custom image.

In some embodiments, the attributes of the goal may include a total amount to be saved, and the executing comprises generating a size of the custom image of the goal for the user via execution of the GenAI model based on the total amount to be saved. In some embodiments, the method may further include retrieving one or more images generated for one or more other users of the software application based on the identifier of the goal, and the generating comprises generating the custom image of the goal for the user via execution of the GenAI model on the one or more images generated for one or more other users. In some embodiments, the custom image of the goal may include at least one of a hologram, a digital image, a video, and a cartoon, which is custom generated by the GenAI model.

FIG. 9B illustrates a method 910 of predicting a user's goal from user data according to example embodiments. For example, the method 910 may be performed by a computing system, a software application, a server, a cloud platform, a combination of systems, and the like.

Referring to FIG. 9B, in 911, the method may include establishing a network connection between a computing system and one or more external sources over a computer network. In 912, the method may include receiving a request from a user via a software application on a user device. In 913, the method may include collecting data about the user from the one or more external sources via the established network connection. In 914, the method may include executing a machine learning model on the collected data about the user to determine the user's goal. In 915, the method may include displaying an image of the goal via a user interface of the software application.

In some embodiments, the establishing may include establishing a secure connection with an external data source prior to collecting the user data from the external data source. In some embodiments, the method may include executing a generative artificial intelligence (GenAI) model on the determined goal of the user to generate a customized image of the goal and display the customized image of the goal via the software application's user interface. In some embodiments, the method may further include training the GenAI model to generate the customized goal image based on a plurality of goal-based images before receiving the user's request.

In some embodiments, the customized image of the goal may include at least one of a hologram, a digital image, a video, and a cartoon. In some embodiments, the collecting may include collecting transaction history data of the user from the one or more external sources and building a user profile with spending attributes of the user learned from the transaction history data. In some embodiments, the method may include converting content from the user profile into a vector prior and inputting the vector to the machine learning model to determine the user's goal. In some embodiments, the method may further include displaying one or more prompts via the user interface, receiving inputs from the user via the one or more prompts on the user interface, and executing the machine learning model on the collected data about the user and the received inputs from the user via the one or prompts to determine the goal of the user.

FIG. 9C illustrates a method 920 of gradually filling in a custom image based on progress toward a goal according to example embodiments. For example, the method 920 may be performed by a computing system, a software application, a server, a cloud platform, a combination of systems, and the like. Referring to FIG. 9C, in 921, the method may include establishing a network connection between the computing system and a data source. In addition, the method may include iteratively performing a sequence of steps, including collecting user data from the data source in 922, executing a generative artificial intelligence (GenAI) model on the collected user data to generate a different image segment in 923, and filling in a different subset of pixels of an image with the generated image segment and display the partially filled in image on a user interface in 924. In some embodiments, the iteratively performing may include iteratively performing the sequence of steps until the image is completely filled in or some other stop condition is detected, such as an end of a predefined time period, etc.

In some embodiments, the executing may include determining the user's goal based on inputs received via the user interface and executing the GenAI model on the determined goal of the user to generate the different image segment. In some embodiments, the filling-in may include detecting how close the user is to reaching the goal based on the user's account activity and filling in an amount of pixels within the image based on how close the user is to reach the goal. In some embodiments, the iteratively performing may include generating a plurality of different image segments, each different in size than each other, via execution of the GenAI model on the collected user data.

In some embodiments, the image may include one or more of a holograph, a still image, and an animated image. In some embodiments, the method may include dividing the image into a plurality of subsets of pixels and filling in a different subset of pixels of the image after each iteration of the GenAI model. In some embodiments, the method further comprises detecting when the image is completely filled in and, in response, delivering the completely filled-in image to a user device of the user.

FIG. 9D illustrates a method 930 of generating pseudo-data structures and images for a plurality of goals according to example embodiments. For example, the method 930 may be performed by a computing system, a software application, a server, a cloud platform, a combination of systems, and the like. Referring to FIG. 9D, in 931, the method may include storing user data in a storage device. In 932, the method may include receiving inputs via prompts displayed on a software application's user interface.

In 933, the method may include identifying a plurality of goals within the received inputs and generating a plurality of data structures corresponding to the plurality of goals, respectively. In 934, the method may include executing a generative artificial intelligence (GenAI) model on the plurality of goals and the stored user data to generate a plurality of custom images of the plurality of goals. In 935, the method may include displaying a plurality of identifiers of the plurality of data structures corresponding to the plurality of goals on a user interface and simultaneously displaying the plurality of custom images next to the plurality goals, respectively.

In some embodiments, executing may include generating the plurality of custom images based on additional user input attributes via the prompts displayed on the user interface. In some embodiments, the method may further include analyzing an account history of the user and generating the plurality of prompts based on the analyzed account history of the user. In some embodiments, the plurality of data structures may include a plurality of temporary accounts within the software application, and the displaying comprises displaying the plurality of images next to the plurality of temporary accounts, respectively.

In some embodiments, the method may further include generating a mapping between the plurality of temporary accounts and an existing account of the user within the software application. In some embodiments, each custom image of a goal may include at least one of a hologram, a digital image, a video, and a cartoon, which is custom generated by the GenAI model. In some embodiments, the method may further include generating distribution rules for distributing funds to the plurality of data structures via the user interface based on additional inputs from the user received via the user interface. In some embodiments, the method may further include receiving incoming funds of the user and distributing the incoming funds to the plurality of data structures based on the generated distribution rules.

Figure 9E:
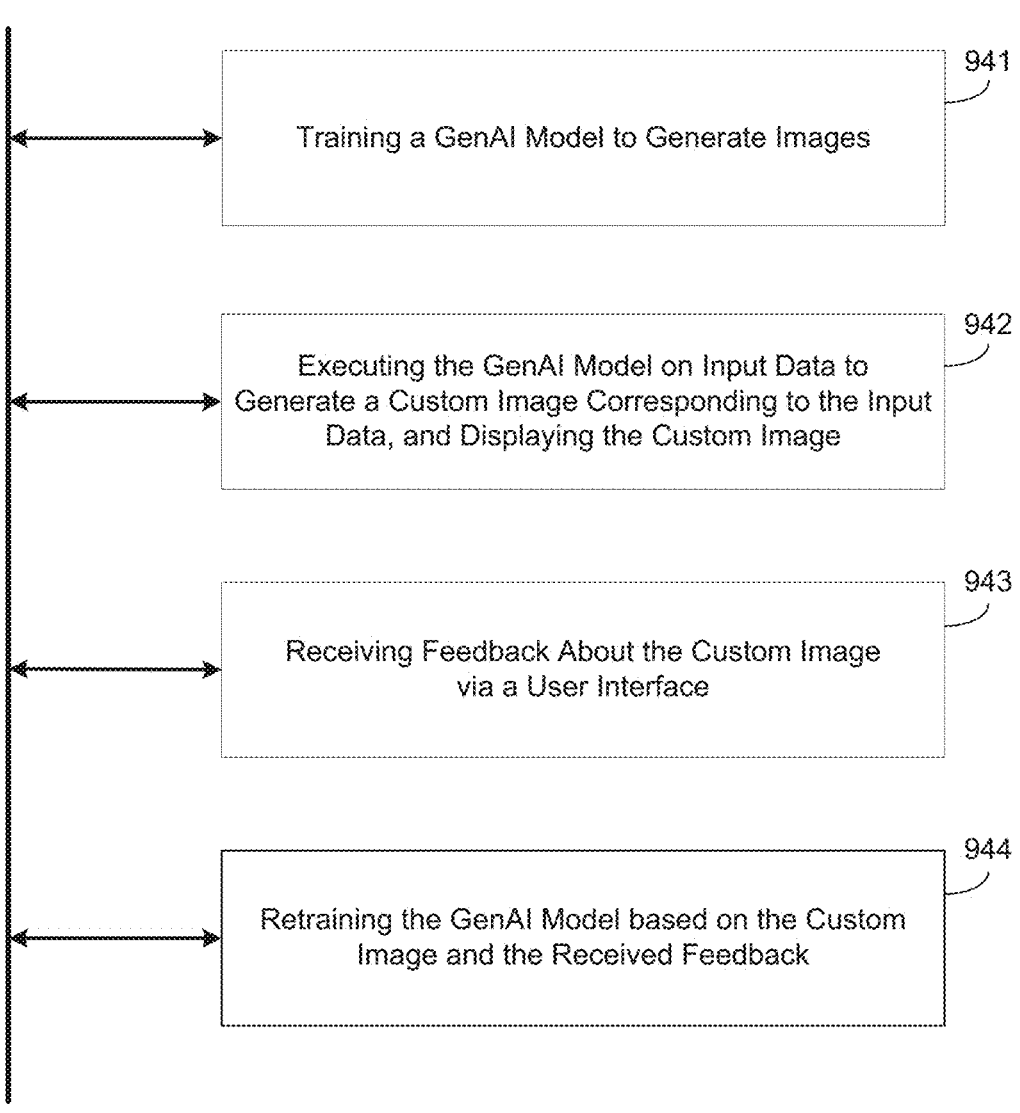
FIG. 9E is a diagram illustrating a method of training a GenAI model to generate custom imagery according to example embodiments.

FIG. 9E illustrates a method 940 of training a GenAI model to generate custom imagery according to example embodiments. As an example, the method 940 may be performed by a computing system, a software application, a server, a cloud platform, a combination of systems, and the like. Referring to FIG. 9E, in 941, the method may include training a generative artificial intelligence (GenAI) model to generate images based on user data using a dataset of images. In 942, the method may include executing the GenAI model based on input data from a software application's user interface to generate an image corresponding to the input data and display the image via a software application's user interface. In 943, the method may include receiving feedback about the image via the user interface. In 944, the method may include retraining the GenAI model based on the generated image and the received feedback about the image via the user interface.

In some embodiments, the executing may include receiving an identifier of a product via the user interface and generating the image via the GenAI model based on the received identifier of the product. In some embodiments, the executing may further include receiving an identifier of the user's goal via the user interface and generating the image via the GenAI model based on the user's received identifier. In some embodiments, the method may further include analyzing an account history of the user, generating a plurality of prompts based on the analyzed account history of the user, and displaying the plurality of prompts on the user interface.

In some embodiments, the method may include receiving the user data via the plurality of prompts displayed on the user interface. In some embodiments, the image may include at least one of a hologram, a digital image, a video, and a cartoon, which is custom-generated by the GenAI model based on the received input data. In some embodiments, the method may include receiving additional user data collected from the user interface, executing the retrained GenAI model based on the additional user data to generate a second image, and displaying the second image via the software application's user interface. In some embodiments, the method may include receiving new feedback about the second image via the user interface and retraining the retrained GenAI model based on the new feedback about the second image.

The above embodiments may be implemented in hardware, a computer program executed by a processor, firmware, or a combination of the above. A computer program may be embodied on a computer-readable medium, such as a storage medium. For example, a computer program may reside in random access memory ("RAM"), flash memory, read-only memory ("ROM"), erasable programmable read-only memory ("EPROM"), electrically erasable programmable read-only memory ("EEPROM"), registers, hard disk, a removable disk, a compact disk read-only memory ("CD-ROM"), or any other form of storage medium known in the art.

An exemplary storage medium may be coupled to the processor such that the processor may read information from, and write information to, the storage medium. In the alternative, the storage medium may be integral to the processor. The processor and the storage medium may reside in an application-specific integrated circuit ("ASIC"). In the alternative, the processor and the storage medium may reside as discrete components. For example, FIG. 10 illustrates an example computer system architecture, which may represent or be integrated into any of the above-described components, etc.

Figure 10:
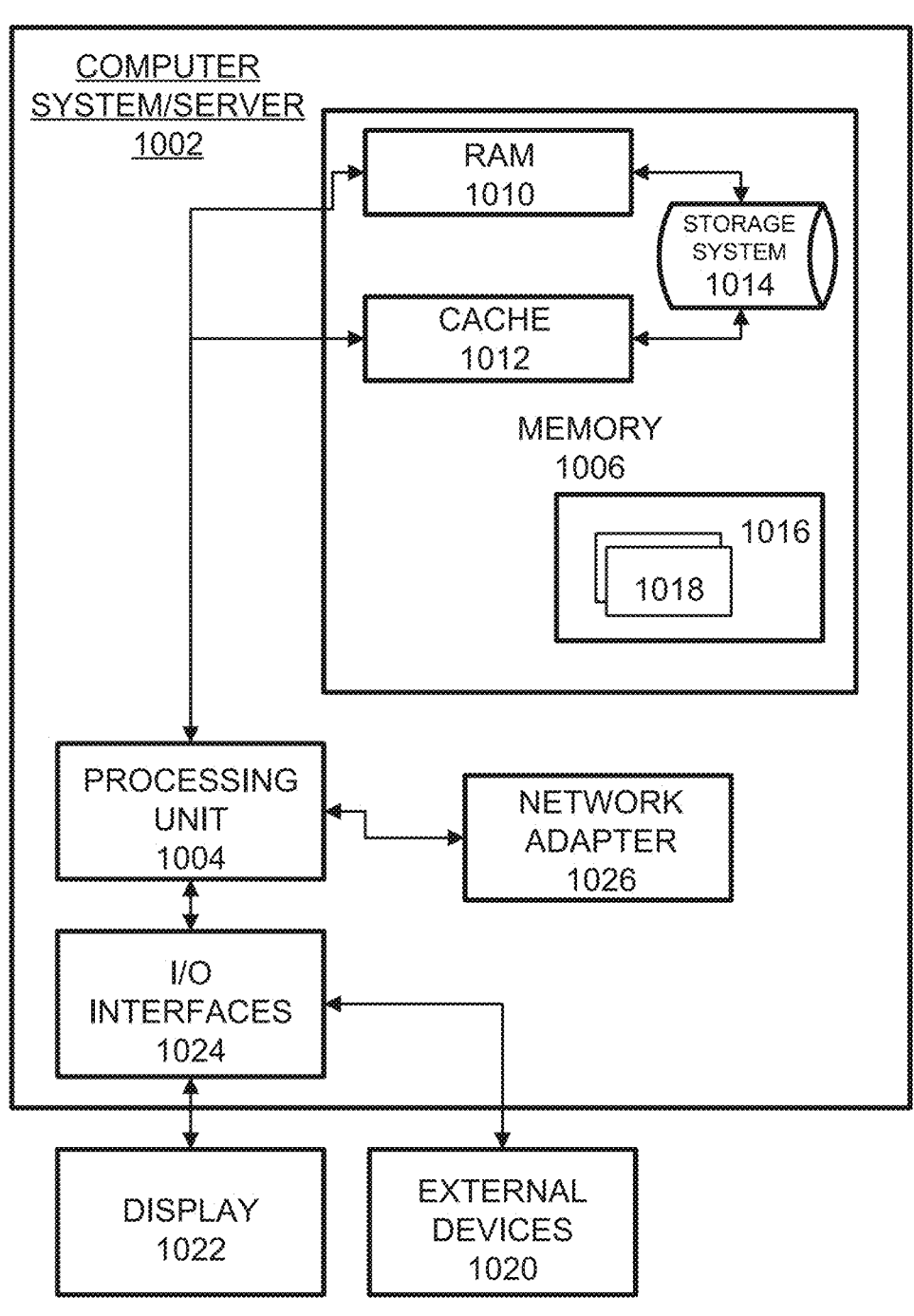
FIG. 10 is a diagram illustrating a computing system that may be used in any of the example embodiments described herein.

FIG. 10 illustrates an example system 1000 that supports one or more example embodiments described and/or depicted herein. The system 1000 comprises a computer system/server 1002, operational with numerous other general-purpose or special-purpose computing system environments or configurations. Examples of well-known computing systems, environments, and/or configurations that may be suitable for use with computer system/server 1002 include but are not limited to, personal computer systems, server computer systems, thin clients, thick clients, hand-held or laptop devices, multiprocessor systems, microprocessor-based systems, set-top boxes, programmable consumer electronics, network PCs, minicomputer systems, mainframe computer systems, and distributed cloud computing environments that include any of the above systems or devices, and the like.

Computer system/server 1002 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 1002 may be practiced in distributed cloud computing environments where tasks are performed by remote processing devices that are linked through a communications network. In a distributed cloud computing environment, program modules may be located in local and remote computer system storage media, including memory storage devices.

As shown in FIG. 10, computer system/server 1002 in the example system 1000 is shown in the form of a general-purpose computing device. The components of computer system/server 1002 may include but are not limited to, one or more processors or processing units (processor 1004), a system memory 1006, and a bus that couples various system components, including system memory 1006 to the processor 1004.

The bus represents one or more of several types of bus structures, including a memory bus or memory controller, a peripheral bus, an accelerated graphics port, and a processor or local bus using various bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 1002 typically includes a variety of computer system-readable media. Such media may be any available media that is accessible by computer system/server 1002, and it includes both volatile and non-volatile media, removable and non-removable media. System memory 1006, in one embodiment, implements the flow diagrams of the other figures. The system memory 1006 can include computer system readable media in the form of volatile memory, such as random-access memory (RAM) 1010 and/or cache memory 1012. Computer system/server 1002 may include other removable/non-removable, volatile/non-volatile computer system storage media. By way of example only, storage system 1014 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to the bus by one or more data media interfaces. As will be further depicted and described below, memory 1006 may include at least one program product with a set (e.g., at least one) of program modules configured to carry out the functions of various embodiments of the application.

Program/utility 1016, having a set (at least one) of program modules 1018, may be stored in memory 1006 by way of example, and not limitation, as well as an operating system, one or more application programs, other program modules, and program data. Each of the operating system, one or more application programs, other program modules, and program data or some combination thereof may include an implementation of a networking environment. Program modules 1018 generally carry out the functions and/or methodologies of various embodiments of the application as described herein.

As will be appreciated by one skilled in the art, aspects of the present application may be embodied as a system, method, or computer program product. Accordingly, aspects of the present application may take the form of an entirely hardware embodiment, an entirely software embodiment (including firmware, resident software, micro-code, etc.), or an embodiment combining software and hardware aspects that may all generally be referred to herein as a "circuit," "module" or "system." Furthermore, aspects of the present application may take the form of a computer program product embodied in one or more computer-readable medium(s) having computer-readable program code embodied thereon.

Computer system/server 1002 may also communicate with one or more external devices 1020 such as a keyboard, a pointing device, a display 1022, etc.; one or more devices that enable a user to interact with computer system/server 1002; and/or any devices (e.g., network card, modem, etc.) that enable computer system/server 1002 to communicate with one or more other computing devices. Such communication can occur via I/O interfaces 1024. Still yet, computer system/server 1002 can communicate with one or more networks, such as a local area network (LAN), a general wide area network (WAN), and/or a public network (e.g., the Internet) via network adapter 1026. As depicted, network adapter 1026 communicates with the other components of computer system/server 1002 via a bus. It should be understood that although not shown, other hardware and/or software components could be used in conjunction with computer system/server 1002. Examples include but are not limited to: microcode, device drivers, redundant processing units, external disk drive arrays, RAID systems, tape drives, and data archival storage systems, etc.

Although an exemplary embodiment of at least one of a system, method, and computer-readable medium has been illustrated in the accompanying drawings and described in the foregoing detailed description, it will be understood that the application is not limited to the embodiments disclosed but is capable of numerous rearrangements, modifications, and substitutions as set forth and defined by the following claims. For example, the system's capabilities of the various figures can be performed by one or more of the modules or components described herein or in a distributed architecture. They may include a transmitter, receiver, or pair of both. For example, all or part of the functionality performed by the individual modules may be performed by one or more of these modules. Further, the functionality described herein may be performed at various times and in relation to various events, internal or external to the modules or components. Also, the information sent between various modules can be sent between the modules via at least one of a data networks, the Internet, a voice network, an Internet Protocol network, a wireless device, a wired device, and/or via a plurality of protocols. Also, the messages sent or received by any of the modules may be sent or received directly and/or via one or more of the other modules.

One skilled in the art will appreciate that a "system" could be embodied as a personal computer, a server, a console, a personal digital assistant (PDA), a cell phone, a tablet computing device, a smartphone, or any other suitable computing device, or combination of devices. Presenting the above-described functions as being performed by a "system" is not intended to limit the scope of the present application in any way but is intended to provide one example of many embodiments. Indeed, methods, systems, and apparatuses disclosed herein may be implemented in localized and distributed forms consistent with computing technology.

It should be noted that some of the system features described in this specification have been presented as modules to more particularly emphasize their implementation independence. For example, a module may be implemented as a hardware circuit comprising custom very large-scale integration (VLSI) circuits or gate arrays, off-the-shelf semiconductors such as logic chips, transistors, or other discrete components. A module may also be implemented in programmable hardware devices such as field programmable gate arrays, programmable array logic, programmable logic devices, graphics processing units, etc.

A module may also be at least partially implemented in software for execution by various types of processors. An identified unit of executable code may, for instance, comprise one or more physical or logical blocks of computer instructions that may, for instance, be organized as an object, procedure, or function. Nevertheless, the executables of an identified module need not be physically located together but may comprise disparate instructions stored in different locations, which, when joined logically together, comprise the module and achieve the stated purpose for the module. Further, modules may be stored on a computer-readable medium, which may be, for instance, a hard disk drive, flash device, random access memory (RAM), tape, or any other such medium used to store data.

Indeed, a module of executable code could be a single instruction or many instructions and may even be distributed over several different code segments, among different programs, and across several memory devices. Similarly, operational data may be identified and illustrated herein within modules and may be embodied in any suitable form and organized within any suitable type of data structure. The operational data may be collected as a single data set or distributed over different locations, including over different storage devices. They may exist, at least partially, merely as electronic signals on a system or network.

It will be readily understood that the components of the application, as generally described and illustrated in the figures herein, may be arranged and designed in a wide variety of different configurations. Thus, the detailed description of the embodiments is not intended to limit the scope of the application as claimed but is merely representative of selected embodiments of the application.

One having ordinary skill in the art will readily understand that the above may be practiced with steps in a different order and/or with hardware elements in configurations that are different from those which are disclosed. Therefore, although the application has been described based on these preferred embodiments, certain modifications, variations, and alternative constructions would be apparent to those of skill in the art.

While preferred embodiments of the present application have been described, it is to be understood that the embodiments described are illustrative only. The scope of the application is to be defined solely by the appended claims when considered with a full range of equivalents and modifications (e.g., protocols, hardware devices, software platforms, etc.) thereto.

What is claimed is:

1. A computing system comprising:
   a memory; and
   a processor coupled to the memory, the processor configured to:
       display a plurality of prompts on a user interface of a software application via a display device on the computing system,
       receive an identifier of a goal associated with an object and a data structure associated with the goal via the user interface,
       execute a generative artificial intelligence (GenAI) model on the identifier of the goal to generate a custom image of the object formed from a collage of integrated images of the object,
       detect an amount of progress towards the goal based on changes to data within the data structure; and
       fill-in a corresponding subset of pixels to reveal a corresponding image segment of the custom image via the user interface based on execution of the GenAI model on the detected amount of progress.

2. The computing system of claim 1, wherein the processor is configured to generate a first partial image of the custom image via the execution of the GenAI model, and display the first partial image of the goal via the user interface of the software application.

3. The computing system of claim 2, wherein the processor is further configured to detect subsequent activity within the data structure after displaying the first partial image, and in response, execute the GenAI model on the subsequent activity to generate a second partial image of the goal with additional data points filled-in in comparison to the first partial image of the goal.

4. The computing system of claim 1, wherein the identifier of the goal comprises an identifier of the object, and the processor is configured to execute the GenAI model on the identifier of the object and based on attributes of the object to generate the custom image.

5. The computing system of claim 4, wherein the attributes of the goal comprise a current amount of data in the data structure, and the processor is configured to execute the GenAI model to fill in a percentage of the custom image based on the current amount of data in the data structure.

6. The computing system of claim 1, wherein the identifier of the goal comprise a total amount, and the processor is further configured to generate a size of the custom image of the goal for the user via execution of the GenAI model based on the total amount.

7. The computing system of claim 1, wherein the processor is further configured to retrieve at least one previously-generated image of the software application based on the identifier of the goal, and generate the custom image of the goal for the user via execution of the GenAI model on the at least one previously-generated image.

8. The computing system of claim 1, wherein the custom image of the goal comprises at least one of a hologram, a digital image, a video, and a cartoon, custom generated by the GenAI model.

9. The computing system of claim 1, wherein the processor is configured to determine a ratio of completion towards the goal based on the changes to data in the data structure, and fill in a ratio of pixels within the custom image to match the ratio of completion towards the goal.

10. A method comprising:
    displaying a plurality of prompts on a user interface of a software application via a display device of a computing system;
    receiving an identifier of a goal associated with an object and a data structure associated with the goal via the user interface;
    executing a generative artificial intelligence (GenAI) model on the identifier of the goal to generate a custom image of the object formed from a collage of integrated images of the object;
    detecting an amount of progress towards the goal based on changes to data within the data structure; and
    filling-in a corresponding subset of pixels to reveal a corresponding image segment of the custom image via the user interface based on execution of the GenAI model on the detected amount of progress.

11. The method of claim 10, wherein the executing comprises generating a first partial image of the custom image via the execution of the GenAI model, and displaying the first partial image of the goal via the user interface of the software application.

12. The method of claim 11, wherein the method further comprises detecting subsequent activity within the data structure after displaying the first partial image, and in response, executing the GenAI model on the subsequent activity to generate a second partial image of the goal with additional data points filled-in in comparison to the first partial image of the goal.

13. The method of claim 10, wherein the identifier of the goal comprises an identifier of the object, and the executing comprises executing the GenAI model on the identifier of the object and based on attributes of the object.

14. The method of claim 13, wherein the identifier of the goal comprise a current amount of data in the data structure, and the executing comprises executing the GenAI model to fill in a percentage of the custom image based on the current amount of data in the data structure.

15. The method of claim 10, wherein the identifier of the goal comprise a total amount, and the executing comprises generating a size of the custom image of the goal for the user via execution of the GenAI model based on the total amount.

16. The method of claim 10, wherein the method further comprises retrieving at least one previously-generated image of the software application based on the identifier of the goal, and the executing comprises generating the custom image of the goal for the user via execution of the GenAI model on the at least one previously-generated image.

17. The method of claim 10, wherein the custom image of the goal comprises at least one of a hologram, a digital image, a video, and a cartoon, custom generated by the GenAI model.

18. A computer-readable medium comprising instructions stored therein which when executed by a processor cause the processor to perform:
    displaying a plurality of prompts on a user interface of a software application via a display device of a computing system;
    receiving an identifier of a goal of associated with an object and a data structure associated with the goal via the user interface;
    executing a generative artificial intelligence (GenAI) model on the identifier of the goal to generate a custom image of the formed from a collage of integrated images of the object;
    detecting an amount of progress towards the goal based on changes to data within the data structure; and
    filling-in a corresponding subset of pixels to reveal a corresponding image segment of the custom image via the user interface based on execution of the GenAI model on the detected amount of progress.

19. The computer-readable medium of claim 18, wherein the executing comprises generating a first partial image of the custom image via the execution of the GenAI model, and displaying the first partial image of the goal via the user interface of the software application.

20. The computer-readable medium of claim 19, wherein the instructions, when executed by the processor, cause the processor to perform detecting subsequent activity within the data structure after displaying the first partial image, and in response, executing the GenAI model on the subsequent activity to generate a second partial image of the goal with additional data points filled-in in comparison to the first partial image of the goal.

* * * * *